(12) United States Patent
Okano et al.

(10) Patent No.: US 8,829,055 B2
(45) Date of Patent: Sep. 9, 2014

(54) BIOFILM FORMATION INHIBITOR COMPOSITION

(75) Inventors: Tetsuya Okano, Wakayama (JP); Shinya Iwasaki, Tokyo (JP); Kazuo Isobe, Wakayama (JP); Eiko Ishizuka, Wakayama (JP)

(73) Assignee: Kao Corporation, Tokyo (JP)

( * ) Notice: Subject to any disclaimer, the term of this patent is extended or adjusted under 35 U.S.C. 154(b) by 1307 days.

(21) Appl. No.: 12/293,994

(22) PCT Filed: Mar. 23, 2007

(86) PCT No.: PCT/JP2007/000288
§ 371 (c)(1),
(2), (4) Date: Nov. 15, 2008

(87) PCT Pub. No.: WO2007/122792
PCT Pub. Date: Nov. 1, 2007

(65) Prior Publication Data
US 2009/0275652 A1    Nov. 5, 2009

(30) Foreign Application Priority Data

| Mar. 23, 2006 | (JP) | 2006-080954 |
| Oct. 20, 2006 | (JP) | 2006-286270 |
| Oct. 20, 2006 | (JP) | 2006-286271 |
| Oct. 20, 2006 | (JP) | 2006-286350 |
| Oct. 20, 2006 | (JP) | 2006-286351 |

(51) Int. Cl.
*A01N 33/08* (2006.01)
*A01N 43/20* (2006.01)
*A01N 37/00* (2006.01)
*A01N 41/10* (2006.01)

(52) U.S. Cl.
USPC ............ 514/668; 514/475; 514/529; 514/708

(58) Field of Classification Search
USPC ........................................................ 514/668
See application file for complete search history.

(56) References Cited

U.S. PATENT DOCUMENTS

| 5,457,083 A * | 10/1995 | Muia et al. .................... 504/128 |
| 2005/0014827 A1 | 1/2005 | Schur |
| 2006/0030539 A1* | 2/2006 | Nick et al. ...................... 514/44 |
| 2007/0185000 A1 | 8/2007 | Zushi et al. |

FOREIGN PATENT DOCUMENTS

| EP | 0733304 A2 | 9/1996 |
| JP | 61-501390 A | 7/1986 |
| JP | 1-501472 A | 5/1989 |
| JP | 8-277202 A | 10/1996 |
| JP | 10-511999 A | 11/1998 |
| JP | 11-512720 A | 11/1999 |
| JP | 2000-504690 A | 4/2000 |
| JP | 2000-191409 A | 7/2000 |
| JP | 2002-205094 A | 7/2002 |
| JP | 2002-524257 A | 8/2002 |
| JP | 2003-160410 A | 6/2003 |
| JP | 2003-342142 A | 12/2003 |
| JP | 2003-535959 A | 12/2003 |
| JP | 2004-018431 A | 1/2004 |
| JP | 2004-513153 A | 4/2004 |
| JP | 2004-155681 A | 6/2004 |
| JP | 2004-231671 A | 8/2004 |
| JP | 2004-525935 A | 8/2004 |
| JP | 2005-47855 A | 2/2005 |
| JP | 2005-154323 A | 6/2005 |
| JP | 2005-187377 A | 7/2005 |
| JP | 2005-289917 A | 10/2005 |
| JP | 2005-537294 A | 12/2005 |
| JP | 2006-23512 A | 1/2006 |
| JP | 2006-36948 A | 2/2006 |
| JP | 2006-176416 A | 7/2006 |
| WO | WO 85/03224 A1 | 8/1985 |
| WO | WO 88/00463 A1 | 1/1988 |
| WO | WO 96/2073 A1 | 7/1996 |
| WO | WO-97/11912 A | 4/1997 |
| WO | WO 97/28687 A1 | 8/1997 |
| WO | WO-00/15562 A1 | 3/2000 |
| WO | WO 01/53216 A1 | 7/2001 |
| WO | WO 01/94513 A1 | 12/2001 |
| WO | WO-02/38181 A2 | 5/2002 |
| WO | WO-02/076928 A2 | 10/2002 |
| WO | WO 2004/012692 A1 | 2/2004 |
| WO | WO 2006/067967 A1 | 6/2006 |

OTHER PUBLICATIONS

FIRP Booklet #E300-A, Teaching Aid in Surfactant Science and Engineering in English, Salager, Jean-Louis, pp. 4 and 7.*
Japanese Office Action issued Jun. 23, 2009, in corresponding Japanese Application No. 2007-76717.
Full Machine English Translation of JP 2005-289917-A (Oct. 20, 2005).
Full Machine English Translation of JP 2003-160410-A (Jun. 3, 2003).
Japanese Notice dated Dec. 20, 2011 for Japanese Application No. 2006-286351.
JPO Office Action, Appl. No. 2006-286271, Aug. 23, 2011 (w/ full English translation).
JPO Office Action, Appl. No. 2006-286350, Aug. 23, 2011 (w/ full English translation).
Japanese Office Action for Application No. 2006-286350 dated May 8, 2012 (with English translation).
Japanese Office Action issued on Oct. 16, 2012 in connection with Japanese Application No. 2006-286350 with an English language translation.
Japanese Office Action issued on Oct. 16, 2012 in connection with Japanese Application No. 2006-286351 with an English language translation.

* cited by examiner

*Primary Examiner* — Sreeni Padmanabhan
*Assistant Examiner* — Timothy E Betton
(74) *Attorney, Agent, or Firm* — Birch, Stewart, Kolasch & Birch, LLP

(57) ABSTRACT

A drug and a composition for inhibiting biofilm formation are provided. A biofilm formation inhibitor composition containing the following component (A): (A) at least one or more selected from compounds represented by Formula (1) to Formula (4): wherein $R^1$ to $R^5$ each represent an alkyl group or the like; EO represents an ethyleneoxy group; p represents an integer from 0 to 5; and m+n represents a number from 0 to 30, or a salt thereof; and (B) a surfactant.

4 Claims, No Drawings

BIOFILM FORMATION INHIBITOR COMPOSITION

FIELD OF THE INVENTION

The present invention relates to a biofilm formation inhibitor composition, and more particularly, to a biofilm formation inhibitor composition inhibiting the formation of a biofilm which is formed of microorganisms and materials produced by microorganisms in various fields to which microorganisms are related, thus preventing the hazard caused by the biofilm.

BACKGROUND OF THE INVENTION

Biofilms, which are also called biological films or slime, refer in general to the structures formed by intracellularly producing polymeric materials such as polysaccharides, proteins and the like by microorganisms that attach themselves on the surface of a material and proliferate in an aqueous system. When biofilms are formed, there occurs hazard caused by microorganisms, and various industrial problems are raised. For instance, when biofilms are formed inside the pipeline of a food processing plant, these biofilms are peeled off, leading to incorporation of foreign substances into food products, as well as causing food borne disease due to the toxins derived from microorganisms. Furthermore, formation of biofilms on metal surfaces is causative of metal corrosion, thereby accelerating decrepitude of facilities.

In addition, with regard to the microbial aggregates which have already formed a biofilm, no sufficient effects are exhibited by microbial control agents such as bactericides or bacteriostatic agents in many cases, as compared with the case with regard to microorganisms which are in the state of being dispersed and floating in an aqueous system. For example, in the aspect of the medical field, there have been many reports in recent years on the cases of in-hospital infection caused by the biofilms formed by microorganisms that survive in narrow interstices or pores of medical instruments. It is well known that the biofilms formed on the teeth in human oral cavity, so-called dental plaques (tooth plaques), are causative of dental caries or gum diseases, and thus, investigation has been conducted on these problems for a long time.

Heretofore, the idea of inhibiting microbial growth by exerting a bactericidal action or bacteriostatic action on microorganisms, particularly bacteria, in order to inhibit biofilms, has been generally examined. Patent Document 1 or Patent Document 2 discloses that the number of bacterial cells is reduced by using fatty acids or aliphatic alcohols, and consequently the adhesion of bacteria onto an object material can be prevented. In particular, Patent Document 1 shows that a composition prepared from an antimicrobial oil phase and emulsifiers as an emulsion exhibits an effect of reducing the number of bacterial cells in a relatively short time, and thus discloses the idea of inhibiting adhesion of bacteria on the surface of the object material on the basis of the phenomenon that the absolute number of bacterial cells per unit volume is decreased. Furthermore, Patent Document 3 discloses a toothpaste composition and the like in which non-aqueous active ingredients such as anti-inflammatory drugs and the like are dissolved in an oily material, while Patent Document 4 discloses a method of preventing establishment of contaminative organisms (barnacles, bacterial slimes or the like) on underwater structures by contacting the contaminative organisms with specific alkylamine derivatives, but neither was effective in inhibiting the formation of biofilms. Furthermore, Patent Document 5 describes a method of inhibiting bacterial adhesion on the surfaces that are immersed in the water, using polyglycol fatty acid esters, and discloses that bacterial adhesion is effectively inhibited at a concentration far lower than the threshold level exhibiting biocidal activity of polyglycol fatty acid esters. Patent Document 6 also discloses an industrial preservative and antifungal agent containing a polyglycerine monofatty acid ester and the like.

Patent Document 1 or 2 describes an evaluation of bactericidal property (reducing the number of bacterial cells by about 4 orders of magnitude) in the case of contacting microorganisms with a bactericidal or antimicrobial composition for a relatively short time of 60 minutes or less. However, since the problem of biofilm takes place over a long time in the order of days to months, it is in fact difficult to draw a conclusion from such short-term evaluation of bactericidal property, on the control of inhibition of biofilm formation. The fatty acids or aliphatic alcohols mentioned as an antibacterial oil phase cannot be said to have a sufficient bactericidal effect on all microorganisms (bacteria), and particularly with regard to gram-negative bacteria which frequently cause problems by forming biofilms, the substances do not have the minimal inhibitory concentration (MIC), which is an index of the bactericidal effect on a long-term basis (Jon J. Kabara ed., Cosmetic and Drug Preservation; Principles and Practice, Fragrance Journal, Ltd., 1990). Moreover, according to an experiment performed by the present inventors, the composition described in Patent Document 1 or Patent Document 2 exhibits, as described therein, a short-term (up to about 3 hours) bactericidal effect on gram-negative bacteria, particularly on *Pseudomonas* or *Serratia*, but there was no indication of bactericidal property, or even of bacteriostatic effects of inhibiting microbial growth, on a long-term basis (1 day or longer), and eventually formation of biofilms was confirmed.

In addition to these, there are bactericidal drugs with a high bactericidal property, having the feature of showing an immediate effect, such as cationic surfactants, hypochlorite and the like having a high bactericidal property. However, since their bactericidal property rapidly disappears in the presence of organic substances in the system, it is difficult to maintain the effect of reducing the number of microbes over a long time as described above.

For these reasons, it was difficult to fundamentally inhibit the formation of biofilms from the viewpoint of bactericide or bacteriostasis of bacteria.

Patent Citation 1: JP-A-2002-524257 (WO 00/15562)
Patent Citation 2: JP-A-2004-513153 (WO 02/038181)
Patent Citation 3: JP-A-2005-289917
Patent Citation 4: JP-A-2004-525935 (WO 02/076928)
Patent Citation 5: JP-A-(Hei) 11-512720 (WO 97/11912)
Patent Citation 6: JP-A-2003-160410

DISCLOSURE OF INVENTION

The present invention provides a biofilm formation inhibitor composition including component (A):

(A) at least one or more selected from the compounds represented by Formula (1) and Formula (2):

Chem. 1

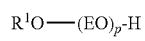

(1)

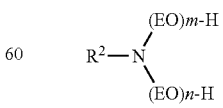

(2)

wherein $R^1$ and $R^2$, which may be identical or different, each represent an alkyl group or an alkenyl group, which is a straight chain or branched chain having 8 to 14 carbon atoms; EO represents an ethyleneoxy group; p represents an integer from 0 to 5; and m and n each represent an average number of added moles, with m+n being a number from 0 to 30;

or a salt thereof, and (B) a surfactant, wherein the weight ratio of the component (A) and the component (B), (A)/(B), is not more than 2.

The present invention is also to provide a method of inhibiting biofilm formation by contacting the biofilm formation inhibitor composition with microorganisms.

In another aspect, the present invention is to provide use of a composition including the following component (A):

(A) at least one or more selected from the compounds represented by Formula (1) and Formula (2):

Chem. 2

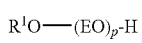
(1)

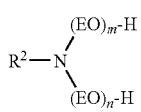
(2)

wherein $R^1$ and $R^2$, which may be identical or different, each represent an alkyl group or an alkenyl group, which is a straight chain or branched chain having 8 to 14 carbon atoms; EO represents an ethyleneoxy group; p represents an integer from 0 to 5; and m and n each represent an average number of added moles, with m+n being a number from 0 to 30;

or a salt thereof, and (B) a surfactant, wherein the weight ratio of the component (A) and the component (B), (A)/(B), is not more than 2, as a biofilm formation inhibitor composition.

In still another aspect, the present invention is to provide a biofilm formation inhibitor composition containing the following component (C):

(C) at least one or more selected from the group consisting of the compounds represented by Formula (3) and Formula (4):

Chem. 3

(3)

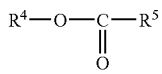
(4)

wherein $R^3$ and $R^4$, which may be identical or different, each represent an alkyl group or an alkenyl group, which is a straight chain or branched chain having 8 to 14 carbon atoms; and $R^5$ represents a hydrogen atom, or a straight chain or branched chain alkyl group having 1 to 3 carbon atoms.

The present invention is also to provide a method of inhibiting biofilm formation by contacting the biofilm formation inhibitor composition with microorganisms.

In another aspect, the present invention is to provide use of the following component (C):

(C) at least one or more selected from the group consisting of the compounds represented by Formula (3) and Formula (4):

Chem. 4

(3)

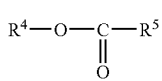
(4)

wherein $R^3$ and $R^4$, which may be identical or different, each represent an alkyl group or an alkenyl group, which is a straight chain or branched chain having 8 to 14 carbon atoms; and $R^5$ represents a hydrogen atom, or a straight chain or branched chain alkyl group having 1 to 3 carbon atoms, as a biofilm formation inhibitor.

DETAILED DESCRIPTION OF THE INVENTION

The present invention provides a biofilm formation inhibitor composition, a method of inhibiting biofilm formation, and use of the composition as a biofilm formation inhibitor.

According to the present invention, the biofilm formation can be inhibited for a prolonged time.

With regard to Formula (1) of the component (A), the alkyl group or alkenyl group represented by $R^1$ may be a straight chain or a branched chain, and from the viewpoint of the biofilm formation inhibitory effect, it preferably has 10 to 12 carbon atoms. The number p of the ethyleneoxy group represented by EO is, from the viewpoint of the biofilm formation inhibitory effect, preferably from 0 to 4, and more preferably 0 to 3, and from the viewpoint of the dispersibility to water, p is preferably 1 to 3.

With regard to Formula (2) of the component (A), the alkyl group or alkenyl group represented by $R^2$ may be a straight chain or a branched chain, and preferably has 10 to 12 carbon atoms. The number of the ethyleneoxy group represented by EO, that is m+n, is preferably 0 to 15, and more preferably 0 to 5. Examples of the salt of the compound represented by the Formula (2) include mineral acid salts such as hydrochloride, sulfate, phosphate and the like, and organic acid salts such as acetate, citrate and the like.

With regard to Formula (3) of the component (C), the alkyl group or alkenyl group represented by $R^3$ may be a straight chain or a branched chain, and preferably has 10 to 12 carbon atoms.

With regard to Formula (4) of the component (C), the alkyl group or alkenyl group represented by $R^4$ may be a straight chain or a branched chain, and preferably has 10 to 12 carbon atoms. Also for the alkyl group of $R^5$, those having 1 or 2 carbon atoms are particularly preferred.

The component (A) or component (C) of the present invention may be favorably present in the system at a weight concentration of 1 ppm or more to manifest a long-term biofilm formation inhibitory effect, preferably 1 to 10,000 ppm from the viewpoint of economic efficiency and effect, more preferably 5 to 10,000 ppm, even more preferably 5 to 2,000 ppm, and even more preferably 10 to 1,000 ppm.

Since the compound of the component (A) of the present invention represented by Formula (1) or Formula (2) has high hydrophobicity and low solubility in water, it becomes possible to use the subject agent more effectively in an aqueous system by rendering the subject agent to exist stably in the aqueous system using the surfactant of the component (B). The compound of the component (C) represented by Formula (3) or Formula (4) exhibits an excellent biofilm formation inhibitory effect by itself, but it is also possible to use the subject agent more effectively in an aqueous system by rendering the subject agent to exist more stably in the aqueous system using the surfactant of the component (B).

Here, the phrase "exist stably in an aqueous system" means a state in which the component (A) or component (C) is emulsified, dispersed or solubilized without undergoing separation on a long-term basis, and it becomes possible to emulsify, disperse or solubilize a larger amount of the component (A) or component (C) per unit volume of the aqueous system.

The type of the surfactant of the component (B) that can be used for the biofilm formation inhibitor composition of the present invention is not particularly limited, but a surfactant which is capable of rendering the component (A) or component (C) to exist stably in an aqueous system is preferred. Particularly from the viewpoint of the capability to emulsify, disperse or solubilize, it is preferable to use anionic surfactants or nonionic surfactants among such surfactants.

Examples of the anionic surfactant include lignin sulfonic acid salts, alkylbenzenesulfonic acid salts, alkylsulfonic acid salts, polyoxyethylene (hereinafter, referred to as POE) alkylsulfonic acid salts, POE alkylphenyl ether sulfonic acid salts, POE alkylphenyl ether phosphoric acid ester salts, POE arylphenyl ether sulfonic acid salts, alkylsulfuric acid ester salts, POE alkylsulfuric acid ester salts, POE arylphenyl ether phosphoric acid ester salts, naphthalenesulfonic acid salts, naphthalenesulfonic acid formalin condensate, POE tribenzylphenyl ether sulfonic acid salts, alkylphosphoric acid salts, POE alkylphosphoric acid salts, POE tribenzylphenyl ether phosphoric acid ester salts, dialkylsulfosuccinic acid salts, fatty acid salts (soap), POE alkyl ether acetic acid salts, and the like. Among these, it is preferable to use alkylsulfuric acid ester salts, POE alkylsulfuric acid ester salts, or POE alkyl ether acetic acid salts. The number of carbon atoms in the alkyl moiety of these anionic surfactants is preferably 10 to 18, and the average number of added moles of ethylene oxide is preferably 0 to 10, and more preferably 0 to 5.

Examples of the nonionic surfactant include monovalent alcohol derivative-type nonionic surfactants such as POE alkyl ethers (with the proviso that the component (A) is excluded), POE alkylphenyl ethers, polyoxypropylene-POE (block or random) alkyl ethers, POE arylphenyl ethers, POE styrenated phenyl ethers, POE tribenzylphenyl ethers, and the like; polyvalent alcohol derivative-type nonionic surfactants such as (poly)glycerin fatty acid esters, sucrose fatty acid esters, sorbitan fatty acid esters, POE sorbitan fatty acid esters, alkylpolyglycosides, and the like; among these, POE alkyl ethers (with the proviso that the component (A) is excluded), (poly)glycerin fatty acid esters, alkylpolyglycosides, sorbitan fatty acid esters, and POE sorbitan fatty acid esters are preferred, with POE alkyl ethers (with the proviso that the component (A) is excluded) being particularly preferred. Inter alia, the HLB value of the POE alkyl ether is more preferably 10 or larger. The number of carbon atoms in the alkyl moiety of POE alkyl ether is preferably 12 to 18, and the average number of added moles of ethylene oxide is particularly 6 or larger.

The surfactant of the component (B) may be used individually, or in combination of two or more species so as to further enhance the capability to emulsify, disperse or solubilize the active ingredient.

In the biofilm formation inhibitor composition, the weight ratio of the component (A) or (C) to the component (B), (A)/(B) or (C)/(B), is preferably 2/1 to 1/100, more preferably 2/1 to 1/50, even more preferably 2/1 to 1/20, and even more preferably 1/1 to 1/10, in view of the long-term biofilm formation inhibitory effect. Moreover, in the case of using the component of the Formula (1) and/or Formula (2), the ratio (A)/(B) is 2 or less in view of the long-term biofilm formation inhibitory effect.

Furthermore, the biofilm formation inhibitor composition contains preferably 0.01 to 10% by weight, more preferably 0.1 to 10% by weight, and even more preferably 0.5 to 5% by weight, of the component (A) or the component (C), and contains preferably 0.1 to 30% by weight, and more preferably 1 to 20% by weight, of the component (B).

The biofilm formation inhibitor composition of the present invention can be used in combination with a bactericide or an antimicrobial agent. In general, when a biofilm is formed, there occurs a situation where it becomes difficult for the bactericide to exert an effect. However, when the biofilm formation is inhibited by the biofilm formation inhibitor composition of the present invention, it becomes possible to sufficiently elicit the efficacy of the bactericide.

The bactericide or antimicrobial agent as described above may be exemplified by a quaternary salt such as benzalkonium chloride, benzethonium chloride, didecyldimethylammonium chloride, cetylpyridinium chloride, chlorhexidine hydrochloride, and the like; chlorhexidine glyconate, polyhexamethylenebiguanidine hydrochloride, triclosan, isopropylmethylphenol, trichlorocarbanilide, ethanol, isopropyl alcohol, or the like.

The biofilm formation inhibitor composition of the present invention can also contain a thickening agent, in order to increase the viscosity of the composition and improve the adhesiveness to the object material.

Furthermore, a chelating agent may be added to the biofilm formation inhibitor composition of the present invention. Examples of the chelating agent include ethylenediamine tetraacetic acid (EDTA), succinic acid, salicylic acid, oxalic acid, malic acid, lactic acid, fumaric acid, tartaric acid, citric acid, gluconic acid, tripolyphosphoric acid, 1-hydroxyethane-1,1-diphosphonic acid, polyacrylic acid, acrylic acid/maleic acid copolymers and salts thereof.

The biofilm formation inhibitor composition of the present invention can take various forms such as liquid, paste, powder, tablet and the like, in accordance with the application. The biofilm formation inhibitor composition may be used as a single formulation containing all of the components as a mixture, but may also be in the form of several divided packages according to the application.

The biofilm formation inhibitor composition of the present invention can be effectively used as a water-diluted system. Certain amounts of water dilutions of the composition are collected, and an object material is immersed therein. In the case where the object material is present extensively, the composition may be sprayed as a mist using a sprayer, or may be sprayed as a froth using a frothing machine. The composition may also be poured over the object material, or may be applied thereon with a brush or the like. In addition to those, a towel or the like may be impregnated with a water dilution of the composition and used to wipe out the object material. As long as the conditions for contacting the composition with microorganisms are satisfied, a water dilution of the composition may be adhered or daubed on the surface where microorganism are possibly present. For the water dilution of the composition, the concentration by weight of the component (A) or component (C) at the time of use is preferably 1 to 10,000 ppm, and more preferably 5 to 10,000 ppm.

For some object materials, it is also possible to smear and spread the composition as a cream or ointment, without diluting the composition in water. In this case, the component (A) or component (C) is provided in the form of being dissolved, dispersed or emulsified in a suitable solvent, and the concentration by weight of the component (A) or component (C) at the time of use is preferably 1 to 10,000 ppm, and more preferably 5 to 10,000 ppm.

The present invention is also to provide a method of inhibiting the formation of a biofilm by contacting the biofilm formation inhibitor composition with microorganisms. Here, it is desirable to carry out the contact between the biofilm formation inhibitor composition and microorganisms continuously. The present invention also provides the use of the component (A) or component (C) as a biofilm formation inhibitor.

The biofilm formation inhibitor composition of the present invention can be used in a wide range of applications where the harm of biofilms is a problem of concern. For example, the composition can be applied to detergents for food or beverage processing plants where the risk of microbial contamination is high. Furthermore, the composition can be applied also to detergents for medical instruments that are susceptible to biofilm formation, such as, for example, endoscope, artificial dialyzer and the like. Moreover, from the viewpoint of being highly safe, the composition can also be used in cleansing agents, toothpastes, oral care products, denture care products and the like for human use.

The following examples further describe and demonstrate embodiments of the present invention. The examples are given solely for the purpose of illustration and are not to be constructed as limitations of the present invention.

EXAMPLES (1) Example of Using the Compound Represented by Formula (1)

Example 1

Blending of a Biofilm Formation Inhibitor Composition, and Verification of Ability to Inhibit Biofilm Formation Component (A) $R^1O\text{-}(EO)_p\text{—}H$ (A-1) C8 alcohol [KALCOL 0898, manufactured by Kao Corporation, $R^1$=C8 alkyl, p=0]
(A-2) C10 alcohol [KALCOL 1098, manufactured by Kao Corporation, $R^1$=C10 alkyl, p=0]
(A-3) C12 alcohol [KALCOL 2098, manufactured by Kao Corporation, $R^1$=C12 alkyl, p=0]
(A-4) C14 alcohol [KALCOL 4098, manufactured by Kao Corporation, $R^1$=C14 alkyl, p=0]
(A-5) Adduct of C12 alcohol and 1 mole of ethylene oxide [NIKKOL BL-1SY, manufactured by Nikko Chemicals Co., Ltd., $R^1$=C12 alkyl, p=1]
(A-6) Adduct of C12 alcohol and 2 moles of ethylene oxide [NIKKOL BL-2SY, manufactured by Nikko Chemicals Co., Ltd., $R^1$=C12 alkyl, p=2]
(A-7) Adduct of C12 alcohol and 3 moles of ethylene oxide [NIKKOL BL-3SY, manufactured by Nikko Chemicals Co., Ltd., $R^1$=C12 alkyl, p=3]
(A-8) Adduct of C12 alcohol and 5 moles of ethylene oxide [NIKKOL BL-5SY, manufactured by Nikko Chemicals Co., Ltd., $R^1$=C12 alkyl, p=5]
(A-9) C12 alcohol [trans-2-dodecen-1-ol, manufactured by Wako Pure Chemical Industries, Ltd., R=C12 alkenyl, p=0]
(A-10) C12 alcohol (secondary) [2-dodecanol, manufactured by Wako Pure Chemical Industries, Ltd., $R^1$=C12 secondary alkyl, p=0]
(A-11) C12 branched alcohol [2-butyl-1-octanol, manufactured by Sigma-Aldrich, Inc., $R^1$=C12 branched alkyl, p=0]

Component (A') $R^{1'}O\text{-}(EO)_p\text{—}H$ (A'-1) C1 alcohol [methanol, manufactured by Wako Pure Chemical Industries, Ltd., $R^{1'}$=C1 alkyl, p=0]
(A'-2) C2 alcohol [ethanol, manufactured by Wako Pure Chemical Industries, Ltd., $R_1$=C2 alkyl, p=0]
(A'-3) C3 alcohol [L-propanol, manufactured by Wako Pure Chemical Industries, Ltd., $R^{1'}$=C3 alkyl, p=0]
(A'-4) C4 alcohol [1-butanol, manufactured by Wako Pure Chemical Industries, Ltd., $R^{1'}$=C4 alkyl, p=0]
(A'-5) C16 alcohol [KALCOL 6098, manufactured by Kao Corporation, $R^{1'}$=C16 alkyl, p=0]
(A'-6) C18 alcohol [KALCOL 8098, manufactured by Kao Corporation, $R^{1'}$=C18 alkyl, p=0]
(A'-7) Adduct of C1 alcohol and 1 mole of ethylene oxide [2-methoxyethanol, manufactured by Wako Pure Chemical Industries, Ltd., $R^{1'}$=C1 alkyl, p=1]
(A'-8) Adduct of C1 alcohol and 2 moles of ethylene oxide [2-(2-methoxyethoxy)ethanol, manufactured by Wako Pure Chemical Industries, Ltd., $R^{1'}$=C1 alkyl, p=2]
(A'-9) Adduct of C2 alcohol and 1 mole of ethylene oxide [2-ethoxyethanol, manufactured by Wako Pure Chemical Industries, Ltd., $R^{1'}$=C2 alkyl, p=1]
(A'-10) Adduct of C2 alcohol and 2 moles of ethylene oxide [2-(2-ethoxyethoxy)ethanol, manufactured by Wako Pure Chemical Industries, Ltd., $R^{1'}$=C2 alkyl, p=2]
(A'-11) Adduct of C4 alcohol and 1 mole of ethylene oxide [2-butoxyethanol, manufactured by Wako Pure Chemical Industries, Ltd., $R^{1'}$=C4 alkyl, p=1]
(A'-12) Adduct of C4 alcohol and 2 moles of ethylene oxide [2-(2-butoxyethoxy)ethanol, manufactured by Wako Pure Chemical Industries, Ltd., $R_1'$=C4 alkyl, p=2]
(A'-13) C20 branched alcohol [2-octyl-1-dodecanol, manufactured by Sigma-Aldrich, Inc., $R^{1'}$=C20 branched alkyl, p=0]
(A'-14) Adduct of C12 alcohol and 8 moles of ethylene oxide [NIKKOL BL-8SY, manufactured by Nikko Chemicals, Ltd., $R^{1'}$=C12alkyl, p=8]

Component (B) Surfactant [the number within the parentheses represents the average number of added moles of ethylene oxide.]

<Anionic Surfactants>
(B-1) Sodium lauryl sulfate [EMAL 0, manufactured by Kao Corporation]
(B-2) Sodium polyoxyethylene(2) lauryl ethersulfate [EMAL 20C, manufactured by Kao Corporation; active ingredient 25% by weight]
(B-3) Sodium polyoxyethylene (4.5) lauryl ether acetate [KAO AKYPO RLM45-NV, manufactured by Kao Corporation; active ingredient 24% by weight]

<Nonionic Surfactants>
(B-4) Polyoxyethylene (6) lauryl ether [EMULGEN 106, manufactured by Kao Corporation]
(B-5) Polyoxyethylene (12) lauryl ether [EMULGEN 120, manufactured by Kao Corporation]
(B-6) Lauryl glucoside [MYDOL 12, manufactured by Kao Corporation]
(B-7) Decyl glyceryl monocaprylate [SY-GLYSTER MCA750, manufactured by SAKAMOTO YAKUHIN KOGYO CO., LTD.]
(B-8) Sorbitan monolaurate [RHEODOLSP-L10, manufactured by Kao Corporation]
(B-9) Polyoxyethylene (6) sorbitan monolaurate [RHEODOL TW-L106, manufactured by Kao Corporation]

(B-10) Polyoxyethylene (20) sorbitan monolaurate [RHEODOL TW-L120, manufactured by Kao Corporation]

The active ingredients were blended on a weight basis such that the concentration of the component (A) or component (A') was fixed at 1% by weight, while the concentration of the component (B) was selected from 1% by weight, 3% by weight, 6% by weight and 10% by weight, with the balance being ion-exchanged water. The blend was diluted using Mueller-Hinton Broth [manufactured by Nippon Becton Dickinson Co., Ltd.], to a concentration of 100 ppm of the component (A) or component (A'), and 2 mL of the dilution was taken and placed on a 24-well microplate [manufactured by ASAHI TECHNO GLASS CORPORATION].

*Pseudomonas* (*Pseudomonas aeruginosa* NBRC 13275), *Serratia* (*Serratia marcescens* NBRC 12648), and *Klebsiella* (*Klebsiella pneumoniae* ATCC 13883) were each pre-cultured using soybean-casein digest agar [SCD Agar Medium; manufactured by Nihon Pharmaceutical Co., Ltd.], at 37 degrees Celsius for 24 hours to form colonies. A very small amount of bacterial clusters from the colonies formed was inoculated into each of the above-described test solutions on the microplate, using a sterilized bamboo skewer. The inoculated solution was incubated at 37 degrees Celsius for 48 hours, then the culture solution was discarded, and the state of formation of the biofilm adhering on the microplate wall was observed by visual evaluation. The state of the biofilm formation was graded such that the state in which the biofilm covered 0 to less than 20% of the plate wall surface was graded A, the state in which the biofilm covered 20% or more to less than 40% was graded B, the state in which the biofilm covered 40% or more to less than 60% was graded C, and the state in which the biofilm covered 60% or more was graded D.

The results are presented in Table 1-1 to Table 1-5.

TABLE 1-1

| | Example product 1 | Example product 2 | Example product 3 | Example product 4 | Example product 5 | Example product 6 | Example product 7 | Example product 8 |
|---|---|---|---|---|---|---|---|---|
| Component (A) $RO-(EO)_n-H$ | | | | | | | | |
| A-1 | 1.0 | 1.0 | 1.0 | | | | | |
| A-2 | | | | 1.0 | 1.0 | 1.0 | 1.0 | 1.0 |
| A-3 | | | | | | | | |
| A-4 | | | | | | | | |
| A-5 | | | | | | | | |
| A-6 | | | | | | | | |
| A-7 | | | | | | | | |
| A-8 | | | | | | | | |
| Surfactant (B) [Anionic Surfactant] | | | | | | | | |
| B-1 | 3.0 | | | 1.0 | | | | |
| B-2 | | 3.0 | | | 3.0 | 6.0 | | |
| B-3 | | | | | | | 3.0 | |
| [Nonionic Surfactant] | | | | | | | | |
| B-4 | | | | | | | | 3.0 |
| B-5 | | | 3.0 | | | | | |
| B-6 | | | | | | | | |
| B-7 | | | | | | | | |
| B-8 | | | | | | | | |
| B-9 | | | | | | | | |
| B-10 | | | | | | | | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition | | | | | | | | |
| *P. aeruginosa* | B | B | B | A | A | A | A | A |
| *S. marcescens* | B | B | B | A | A | A | A | A |
| *K. neumoniae* | B | B | B | A | A | A | A | A |

| | Example product 9 | Example product 10 | Example product 11 | Example product 12 | Example product 13 | Example product 14 | Example product 15 | Example product 16 |
|---|---|---|---|---|---|---|---|---|
| Component (A) $RO-(EO)_n-H$ | | | | | | | | |
| A-1 | | | | | | | | |
| A-2 | 1.0 | 1.0 | | | | | | |
| A-3 | | | 1.0 | 1.0 | 1.0 | 1.0 | 1.0 | 1.0 |
| A-4 | | | | | | | | |
| A-5 | | | | | | | | |
| A-6 | | | | | | | | |
| A-7 | | | | | | | | |
| A-8 | | | | | | | | |

TABLE 1-1-continued

| | | | | | | | | |
|---|---|---|---|---|---|---|---|---|
| Surfactant (B) [Anionic Surfactant] | | | | | | | | |
| B-1 | | | 3.0 | 6.0 | | | | |
| B-2 | | | | | | | | |
| B-3 | | | | | | | | |
| [Nonionic Surfactant] | | | | | | | | |
| B-4 | | | | | 1.0 | 3.0 | | |
| B-5 | 1.0 | | | | | | 3.0 | 10.0 |
| B-6 | | | | | | | | |
| B-7 | | | | | | | | |
| B-8 | | | | | | | | |
| B-9 | | 3.0 | | | | | | |
| B-10 | | | | | | | | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition | | | | | | | | |
| P. aeruginosa | A | A | A | A | A | A | A | A |
| S. marcescens | A | A | A | A | A | A | A | A |
| K. neumoniae | A | A | A | A | A | A | A | A |

TABLE 1-2

| | Example product 17 | Example product 18 | Example product 19 | Example product 20 | Example product 21 | Example product 22 | Example product 23 | Example product 24 | Example product 25 |
|---|---|---|---|---|---|---|---|---|---|
| Component (A) RO-(EO)$_n$-H | | | | | | | | | |
| A-1 | | | | | | | | | |
| A-2 | | | | | | | | | |
| A-3 | 1.0 | | | | | | | | |
| A-4 | | 1.0 | 1.0 | 1.0 | | | | | |
| A-5 | | | | | 1.0 | 1.0 | 1.0 | 1.0 | |
| A-6 | | | | | | | | | 1.0 |
| A-7 | | | | | | | | | |
| Surfactant (B) [Anionic Surfactant] | | | | | | | | | |
| B-1 | | | | | 3.0 | | | | |
| B-2 | | 3.0 | | | | | | | 3.0 |
| B-3 | | | | | | | | | |
| [Nonionic Surfactant] | | | | | | | | | |
| B-4 | | | | | | 3.0 | | | |
| B-5 | | | | | | | 3.0 | 6.0 | |
| B-6 | | | | | | | | | |
| B-7 | | | 10.0 | | | | | | |
| B-8 | | | | 3.0 | | | | | |
| B-9 | | | | | | | | | |
| B-10 | 6.0 | | | | | | | | |
| Ion-Exchanged Water | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 |
| State of Biofilm Inhibition | | | | | | | | | |
| P. aeruginosa | A | B | B | B | A | A | A | A | A |
| S. marcescens | A | B | B | B | A | A | A | A | A |
| K. pneumoniae | A | B | B | B | A | A | A | A | A |

TABLE 1-2-continued

|  | Example product 26 | Example product 27 | Example product 28 | Example product 29 | Example product 30 | Example product 31 | Example product 32 | Example product 33 | Example product 34 |
|---|---|---|---|---|---|---|---|---|---|
| Component (A) RO-(EO)$_n$-H | | | | | | | | | |
| A-1 | | | | | | | | | |
| A-2 | | | | | | | | | |
| A-3 | | | | | | | | | |
| A-4 | | | | | | | | | |
| A-5 | | | | | | | | | |
| A-6 | 1.0 | 1.0 | 1.0 | | | | | | |
| A-7 | | | | 1.0 | 1.0 | 1.0 | 1.0 | 1.0 | 1.0 |
| Surfactant (B) [Anionic Surfactant] | | | | | | | | | |
| B-1 | | | | 6.0 | | | | | |
| B-2 | | | | | | | | | |
| B-3 | | | | | | | | | |
| [Nonionic Surfactant] | | | | | | | | | |
| B-4 | | | | | | | | | |
| B-5 | 3.0 | | | | 10.0 | | | | |
| B-6 | | 3.0 | | | | 3.0 | | | |
| B-7 | | | | | | | 6.0 | | |
| B-8 | | | | | | | | 3.0 | |
| B-9 | | | | | | | | | 3.0 |
| B-10 | | | 3.0 | | | | | | |
| Ion-Exchanged Water | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 |
| State of Biofilm Inhibition | | | | | | | | | |
| P. aeruginosa | A | A | A | A | A | A | A | A | A |
| S. marcescens | A | A | A | A | A | A | A | A | A |
| K. pneumoniae | A | A | A | A | A | A | A | A | A |

TABLE 1-3

|  | Example product 35 | Example product 36 | Example product 37 | Example product 38 | Example product 39 | Example product 40 | Example product 41 | Example product 42 |
|---|---|---|---|---|---|---|---|---|
| Component (A) RO-(EO)$_n$-H | | | | | | | | |
| A-8 | 1.0 | 1.0 | 1.0 | | | | | |
| A-9 | | | | 1.0 | 1.0 | 1.0 | | |
| A-10 | | | | | | | 1.0 | 1.0 |
| A-11 | | | | | | | | |
| Surfactant (B) [Anionic Surfactant] | | | | | | | | |
| B-1 | | | | 6.0 | | | | |
| B-2 | | | | | | | | 6.0 |
| B-3 | | | | | | | | |
| [Nonionic Surfactant] | | | | | | | | |
| B-4 | | | | | 3.0 | | | |
| B-5 | 3.0 | | | | | 3.0 | 6.0 | 3.0 |
| B-6 | | 3.0 | | | | | | |
| B-7 | | | | | | | | |
| B-8 | | | | | | | | |
| B-9 | | | | | | | | |
| B-10 | | | | | | | 3.0 | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |

TABLE 1-3-continued

State of Biofilm Inhibition

|  |  |  |  |  |  |  |  |  |
|---|---|---|---|---|---|---|---|---|
| P. aeruginosa | A | A | B | A | A | A | A | A |
| S. marcescens | B | B | B | A | A | A | A | A |
| K. pneumoniae | A | B | B | A | A | A | A | A |

|  | Example product 43 | Example product 44 | Example product 45 | Example product 46 |
|---|---|---|---|---|
| Component (A) |  |  |  |  |
| A-8 |  |  |  |  |
| A-9 |  |  |  |  |
| A-10 | 1.0 |  |  |  |
| A-11 |  | 1.0 | 1.0 | 1.0 |
| Surfactant (B) |  |  |  |  |
| [Anionic Surfactant] |  |  |  |  |
| B-1 |  | 3.0 |  |  |
| B-2 |  |  |  |  |
| B-3 | 3.0 |  |  |  |
| [Nonionic Surfactant] |  |  |  |  |
| B-4 |  |  |  |  |
| B-5 |  |  |  |  |
| B-6 |  |  | 6.0 |  |
| B-7 |  |  |  |  |
| B-8 |  |  |  |  |
| B-9 |  |  |  |  |
| B-10 |  |  |  | 3.0 |
| Ion-Exchanged Water | Balance | Balance | Balance | Balance |
| Total | 100.0 | 100.0 | 100.0 | 100.0 |
| State of Biofilm Inhibition |  |  |  |  |
| P. aeruginosa | A | A | A | A |
| S. marcescens | A | A | A | A |
| K. pneumoniae | A | A | A | A |

TABLE 1-4

|  | Comparative Product 1 | Comparative Product 2 | Comparative Product 3 | Comparative Product 4 | Comparative Product 5 | Comparative Product 6 | Comparative Product 7 | Comparative Product 8 |
|---|---|---|---|---|---|---|---|---|
| Component (A') |  |  |  |  |  |  |  |  |
| R'O-(EO)$_n$-H |  |  |  |  |  |  |  |  |
| A'-1 | 1.0 | 1.0 |  |  |  |  |  |  |
| A'-2 |  |  | 1.0 | 1.0 | 1.0 |  |  |  |
| A'-3 |  |  |  |  |  | 1.0 | 1.0 | 1.0 |
| A'-4 |  |  |  |  |  |  |  |  |
| A'-5 |  |  |  |  |  |  |  |  |
| A'-6 |  |  |  |  |  |  |  |  |
| A'-7 |  |  |  |  |  |  |  |  |
| A'-8 |  |  |  |  |  |  |  |  |
| A'-9 |  |  |  |  |  |  |  |  |
| A'-10 |  |  |  |  |  |  |  |  |
| A'-11 |  |  |  |  |  |  |  |  |
| A'-12 |  |  |  |  |  |  |  |  |
| Surfactant (B) |  |  |  |  |  |  |  |  |
| [Anionic Surfactant] |  |  |  |  |  |  |  |  |
| B-1 | 6.0 |  |  |  |  |  |  |  |
| B-2 |  |  | 3.0 |  |  | 1.0 |  |  |
| B-3 |  |  |  |  |  |  |  |  |
| [Nonionic Surfactant] |  |  |  |  |  |  |  |  |
| B-4 |  |  |  |  |  |  |  |  |
| B-5 |  | 3.0 |  | 3.0 |  |  | 3.0 |  |
| B-6 |  |  |  |  | 6.0 |  |  |  |

TABLE 1-4-continued

|  |  |  |  |  |  |  |  |  |
|---|---|---|---|---|---|---|---|---|
| B-7 |  |  |  |  |  |  | 10.0 |  |
| B-8 |  |  |  |  |  |  |  |  |
| B-9 |  |  |  |  |  |  |  |  |
| B-10 |  |  |  |  |  |  |  |  |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition |  |  |  |  |  |  |  |  |
| *P. aeruginosa* | D | D | D | D | D | D | D | D |
| *S. marcescens* | D | D | D | D | D | D | D | D |
| *K. pneumoniae* | D | D | D | D | D | D | D | D |

|  | Comparative Product 9 | Comparative Product 10 | Comparative Product 11 | Comparative Product 12 | Comparative Product 13 | Comparative Product 14 | Comparative Product 15 | Comparative Product 16 |
|---|---|---|---|---|---|---|---|---|
| Component (A') R'O-(EO)$_n$-H |  |  |  |  |  |  |  |  |
| A'-1 |  |  |  |  |  |  |  |  |
| A'-2 |  |  |  |  |  |  |  |  |
| A'-3 |  |  |  |  |  |  |  |  |
| A'-4 | 1.0 | 1.0 |  |  |  |  |  |  |
| A'-5 |  |  | 1.0 | 1.0 |  |  |  |  |
| A'-6 |  |  |  |  | 1.0 | 1.0 |  |  |
| A'-7 |  |  |  |  |  |  | 1.0 | 1.0 |
| A'-8 |  |  |  |  |  |  |  |  |
| A'-9 |  |  |  |  |  |  |  |  |
| A'-10 |  |  |  |  |  |  |  |  |
| A'-11 |  |  |  |  |  |  |  |  |
| A'-12 |  |  |  |  |  |  |  |  |
| Surfactant (B) [Anionic Surfactant] |  |  |  |  |  |  |  |  |
| B-1 |  |  |  |  |  |  |  |  |
| B-2 |  |  |  |  |  |  |  |  |
| B-3 |  |  |  |  |  |  |  |  |
| [Nonionic Surfactant] |  |  |  |  |  |  |  |  |
| B-4 |  |  |  |  |  |  |  |  |
| B-5 | 3.0 |  | 3.0 |  | 3.0 |  | 3.0 |  |
| B-6 |  |  |  |  |  |  |  |  |
| B-7 |  | 10.0 |  |  |  |  |  |  |
| B-8 |  |  |  |  |  |  |  | 3.0 |
| B-9 |  |  |  | 3.0 |  |  |  |  |
| B-10 |  |  |  |  |  | 10.0 |  |  |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition |  |  |  |  |  |  |  |  |
| *P. aeruginosa* | D | D | C | C | D | D | D | D |
| *S. marcescens* | D | D | C | C | D | D | D | D |
| *K. pneumoniae* | D | D | C | C | D | D | D | D |

TABLE 1-5

| | Comparative Product 17 | Comparative Product 18 | Comparative Product 19 | Comparative Product 20 | Comparative Product 21 | Comparative Product 22 |
|---|---|---|---|---|---|---|
| Component (A') R'O-(EO)$_n$-H | | | | | | |
| A'-1 | | | | | | |
| A'-2 | | | | | | |
| A'-3 | | | | | | |
| A'-4 | | | | | | |
| A'-5 | | | | | | |
| A'-6 | | | | | | |
| A'-7 | | | | | | |
| A'-8 | 1.0 | 1.0 | | | | |
| A'-9 | | | 1.0 | 1.0 | | |
| A'-10 | | | | | 1.0 | 1.0 |
| A'-11 | | | | | | |
| A'-12 | | | | | | |
| A'-13 | | | | | | |
| A'-14 | | | | | | |
| Surfactant (B) [Anionic Surfactant] | | | | | | |
| B-1 | 6.0 | | | | | |
| B-2 | | | 3.0 | | | |
| B-3 | | | | | 3.0 | |
| [Nonionic Surfactant] | | | | | | |
| B-4 | | | | | | |
| B-5 | | 3.0 | | 3.0 | | 3.0 |
| B-6 | | | | | | |
| B-7 | | | | | | |
| B-8 | | | | | | |
| B-9 | | | | | | |
| B-10 | | | | | | |
| Ion-Exchanged Water | Balance | Balance | Balance | Balance | Balance | Balance |
| Total | 100.0 | 100.0 | 100.0 | 100.0 | 100.0 | 100.0 |
| State of Biofilm Inhibition | | | | | | |
| *P. aeruginosa* | D | D | D | D | D | D |
| *S. marcescens* | D | D | D | D | D | D |
| *K. pneumoniae* | D | D | D | D | D | D |

| | Comparative Product 23 | Comparative Product 24 | Comparative Product 25 | Comparative Product 26 | Comparative Product 27 | Comparative Product 28 |
|---|---|---|---|---|---|---|
| Component (A') R'O-(EO)$_n$-H | | | | | | |
| A'-1 | | | | | | |
| A'-2 | | | | | | |
| A'-3 | | | | | | |
| A'-4 | | | | | | |
| A'-5 | | | | | | |
| A'-6 | | | | | | |
| A'-7 | | | | | | |
| A'-8 | | | | | | |
| A'-9 | | | | | | |
| A'-10 | | | | | | |
| A'-11 | 1.0 | 1.0 | | | | |
| A'-12 | | | 1.0 | 1.0 | | |
| A'-13 | | | | | 1.0 | 1.0 |
| A'-14 | | | | | | |
| Surfactant (B) [Anionic Surfactant] | | | | | | |
| B-1 | 3.0 | | 3.0 | | | |
| B-2 | | | | | | |
| B-3 | | | | | | |
| [Nonionic Surfactant] | | | | | | |
| B-4 | | | | | | |
| B-5 | | 3.0 | | 3.0 | | |

TABLE 1-5-continued

| | | | | | | |
|---|---|---|---|---|---|---|
| B-6 | | | | | 3.0 | |
| B-7 | | | | | | |
| B-8 | | | | | | 3.0 |
| B-9 | | | | | | |
| B-10 | | | | | | |
| Ion-Exchanged Water | Balance | Balance | Balance | Balance | Balance | Balance |
| Total | 100.0 | 100.0 | 100.0 | 100.0 | 101.0 | 102.0 |
| State of Biofilm Inhibition | | | | | | |
| P. aeruginosa | D | D | D | D | D | D |
| S. marcescens | D | D | D | D | D | D |
| K. pneumoniae | D | D | D | D | D | D |

| | Comparative Product 29 | Comparative Product 30 |
|---|---|---|
| Component (A') R'O-(EO)$_n$-H | | |
| A'-1 | | |
| A'-2 | | |
| A'-3 | | |
| A'-4 | | |
| A'-5 | | |
| A'-6 | | |
| A'-7 | | |
| A'-8 | | |
| A'-9 | | |
| A'-10 | | |
| A'-11 | | |
| A'-12 | | |
| A'-13 | | |
| A'-14 | 1.0 | 1.0 |
| Surfactant (B) [Anionic Surfactant] | | |
| B-1 | | |
| B-2 | | |
| B-3 | | |
| [Nonionic Surfactant] | | |
| B-4 | | |
| B-5 | | |
| B-6 | | |
| B-7 | | |
| B-8 | | |
| B-9 | 3.0 | |
| B-10 | | 6.0 |
| Ion-Exchanged Water | Balance | Balance |
| Total | 100.0 | 100.0 |
| State of Biofilm Inhibition | | |
| P. aeruginosa | C | C |
| S. marcescens | D | D |
| K. pneumoniae | C | C |

Example 2

Test For Reduction of Biofilm Production in Large-Volume Plastic Cup

Pseudomonas (*Pseudomonas aeruginosa* NBRC 13275) was pre-cultured using soybean-casein digest agar [SCD Agar Medium; manufactured by Nihon Pharmaceutical Co., Ltd.] at 37 degrees Celsius for 24 hours. The colonies grown on the medium were scraped off and suspended in 10 mM sterile phosphate buffer (pH 7.2). The resultant suspension was washed by centrifuging twice at 5,000×g for 15 minutes at 10 degrees Celsius, and then suspended again in 10 mM sterile phosphate buffer (pH 7.2) to prepare a bacterial suspension in which the bacterial concentration was adjusted to 1.0 as the absorbance at 600 nm (OD$_{600}$=1.0). Thereafter, 100 mL of Mueller-Hinton Broth [manufactured by Nippon Becton Dickinson, Co., Ltd.] and each of 15 species of the testing drugs selected from Example 1 were introduced into a 200-mL sterile screw cup [manufactured by EIKENKIZAI CO., LTD.] and mixed thoroughly. The concentration of the component (A) or component (A') was adjusted to 5 ppm, 10 ppm, 50 ppm, 100 ppm or 500 ppm, and then 0.1 mL of the bacterial suspension prepared as described above was inoculated thereinto. Furthermore, as a control, a test section was simultaneously provided in which bacteria were inoculated as described above in Mueller-Hinton Broth with no added drugs.

These were statically cultured at 37 degrees Celsius, and at the designated time points of 1 day, 2 days, 3 days and 5 days after the initiation of culture, the number of bacterial cells was measured, and the biofilm formed inside the cup was observed by visual evaluation. Subsequently, the culture solutions were centrifuged at 10,000×g for 30 minutes at 5 degrees Celsius, and the respective precipitates were removed, dried in a vacuum desiccator for 24 hours, and weighed, with the weight thus measured being taken as the weight of the biofilm produced in the culture solution. Furthermore, the state of the biofilm formation was graded such that the state in which no biofilm was confirmed in the cup was graded A; the state in which the formation of a biofilm started inside the cup at the air-liquid interface was graded B, and the state in which a biofilm was formed to extend from the air-liquid interface down to the culture solution was graded C.

The results are presented in Table 2-1-1 to Table 2-4-5.

TABLE 2-1-1

|  | Control | | | Example product 1 Concentration of Component (A) | | | | | |
|---|---|---|---|---|---|---|---|---|---|
|  | — | | | 5 ppm | | | 10 ppm | | |
|  | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 32.4 | B | 8.0 | 20.6 | B | 7.9 | 18.3 | B | 8.1 |
| After 2 Days of Culture | 49.9 | C | 8.2 | 23.1 | B | 8.3 | 20.4 | B | 8.0 |
| After 3 Days of Culture | 51.3 | C | 8.4 | 28.4 | B | 8.1 | 28.1 | B | 7.9 |
| After 5 Days of Culture | 63.9 | C | 8.5 | 31.9 | B | 8.6 | 30.9 | B | 8.2 |

|  | Example product 1 Concentration of Component (A) | | | | | | | | |
|---|---|---|---|---|---|---|---|---|---|
|  | 50 ppm | | | 100 ppm | | | 500 ppm | | |
|  | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 10.1 | A | 7.8 | 11.0 | A | 7.9 | 10.5 | A | 7.8 |
| After 2 Days of Culture | 17.6 | B | 8.0 | 16.8 | B | 7.9 | 15.8 | B | 7.9 |
| After 3 Days of Culture | 26.1 | B | 8.1 | 20.8 | B | 8.1 | 19.9 | B | 7.8 |
| After 5 Days of Culture | 29.7 | B | 8.0 | 28.2 | B | 8.3 | 24.1 | B | 8.0 |

TABLE 2-1-2

|  | Example product 4 Concentration of Component (A) | | | | | | | | | | | | | | |
|---|---|---|---|---|---|---|---|---|---|---|---|---|---|---|---|
|  | 5 ppm | | | 10 ppm | | | 50 ppm | | | 100 ppm | | | 500 ppm | | |
|  | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.5 | A | 7.5 | 1.7 | A | 7.6 | 1.7 | A | 7.7 | 1.8 | A | 7.9 | 1.9 | A | 7.4 |

TABLE 2-1-2-continued

Example product 4
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 2 Days of Culture | 4.9 | A | 7.8 | 2.8 | A | 7.9 | 2.8 | A | 7.5 | 2.9 | A | 7.8 | 3.1 | A | 7.6 |
| After 3 Days of Culture | 20.7 | B | 7.8 | 9.8 | A | 8.1 | 4.3 | A | 7.8 | 3.8 | A | 7.8 | 4.5 | A | 7.5 |
| After 5 Days of Culture | 31.0 | B | 7.8 | 27.1 | B | 7.9 | 13.7 | B | 7.6 | 7.9 | A | 7.6 | 6.4 | A | 7.8 |

TABLE 2-1-3

Example product 9
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.6 | A | 7.6 | 1.8 | A | 7.5 | 1.8 | A | 7.5 | 1.9 | A | 7.3 | 1.9 | A | 7.4 |
| After 2 Days of Culture | 4.9 | A | 7.4 | 3.6 | A | 7.8 | 3.0 | A | 7.4 | 3.4 | A | 7.5 | 2.7 | A | 7.4 |
| After 3 Days of Culture | 19.8 | B | 7.8 | 9.8 | A | 7.8 | 4.5 | A | 7.6 | 3.8 | A | 7.5 | 3.8 | A | 7.8 |
| After 5 Days of Culture | 33.2 | B | 7.9 | 32.6 | B | 7.4 | 13.2 | A | 7.5 | 6.3 | A | 7.7 | 5.2 | A | 7.6 |

TABLE 2-1-4

Example product 12
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.8 | A | 7.4 | 1.8 | A | 7.6 | 1.9 | A | 7.4 | 2.1 | A | 7.2 | 2.0 | A | 7.8 |
| After 2 Days of Culture | 5.6 | A | 7.9 | 3.2 | A | 7.5 | 2.8 | A | 7.8 | 2.6 | A | 7.6 | 3.1 | A | 7.6 |
| After 3 Days of Culture | 23.6 | B | 7.8 | 9.9 | A | 7.6 | 5.6 | A | 7.6 | 6.8 | A | 7.5 | 4.5 | A | 7.7 |
| After 5 Days of Culture | 36.1 | B | 7.8 | 31.1 | B | 7.9 | 14.4 | B | 7.5 | 10.1 | A | 7.4 | 7.9 | A | 7.5 |

TABLE 2-1-5

Example product 14
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.4 | A | 7.6 | 1.9 | A | 7.8 | 1.7 | A | 7.7 | 1.8 | A | 7.3 | 1.8 | A | 7.6 |
| After 2 Days of Culture | 5.5 | A | 7.9 | 3.5 | A | 7.8 | 3.5 | A | 7.9 | 3.7 | A | 7.7 | 3.5 | A | 7.8 |
| After 3 Days of Culture | 28.7 | B | 7.5 | 10.0 | A | 7.6 | 5.1 | A | 7.6 | 5.2 | A | 7.6 | 4.3 | A | 7.5 |
| After 5 Days of Culture | 35.2 | B | 7.6 | 30.2 | B | 7.6 | 11.1 | A | 7.8 | 7.1 | A | 7.8 | 5.6 | A | 7.4 |

*$Log_{10}$CFU/mL

TABLE 2-2-1

Example product 15
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 3.1 | A | 7.4 | 1.8 | A | 7.1 | 1.7 | A | 7.4 | 1.9 | A | 7.4 | 1.7 | A | 7.3 |
| After 2 Days of Culture | 6.2 | A | 7.6 | 3.8 | A | 7.6 | 3.1 | A | 7.9 | 3.4 | A | 7.3 | 3.1 | A | 7.4 |
| After 3 Days of Culture | 27.6 | B | 7.9 | 10.7 | A | 7.6 | 6.3 | A | 7.4 | 5.7 | A | 7.5 | 4.7 | A | 7.2 |
| After 5 Days of Culture | 35.8 | B | 7.8 | 32.1 | B | 7.6 | 11.1 | B | 7.8 | 10.8 | A | 7.8 | 8.0 | A | 7.1 |

TABLE 2-2-2

Example product 19
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 18.7 | B | 7.8 | 18.0 | B | 8.0 | 11.2 | A | 7.5 | 10.7 | A | 7.6 | 12.1 | A | 8.0 |
| After 2 Days of Culture | 22.9 | B | 8.1 | 22.1 | B | 7.8 | 18.6 | B | 8.3 | 16.6 | B | 7.9 | 16.4 | B | 7.7 |
| After 3 Days of Culture | 27.6 | B | 8.3 | 25.9 | B | 7.4 | 25.3 | B | 8.2 | 23.7 | B | 8.4 | 21.0 | B | 7.9 |
| After 5 Days of Culture | 37.2 | B | 8.4 | 29.8 | B | 7.9 | 28.1 | B | 8.4 | 29.5 | B | 8.4 | 26.4 | B | 7.8 |

TABLE 2-2-3

Example product 23
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 3.2 | A | 7.1 | 2.9 | A | 7.5 | 2.2 | A | 7.2 | 2.4 | A | 7.9 | 1.9 | A | 7.2 |
| After 2 Days of Culture | 7.3 | A | 7.5 | 8.1 | A | 7.5 | 3.8 | A | 7.6 | 5.3 | A | 7.8 | 5.8 | A | 7.4 |
| After 3 Days of Culture | 22.1 | B | 7.6 | 18.6 | B | 7.1 | 7.1 | A | 7.8 | 6.9 | A | 7.6 | 10.1 | A | 7.6 |
| After 5 Days of Culture | 29.8 | B | 7.7 | 22.6 | B | 7.2 | 19.0 | B | 7.8 | 17.7 | B | 7.7 | 16.7 | B | 7.1 |

TABLE 2-2-4

Example product 26
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 5.4 | A | 6.9 | 3.1 | A | 7.3 | 2.8 | A | 7.2 | 2.6 | A | 7.3 | 2.4 | A | 7.3 |
| After 2 Days of Culture | 6.9 | A | 7.4 | 5.1 | A | 7.7 | 4.6 | A | 7.3 | 5.1 | A | 7.5 | 4.6 | A | 7.4 |
| After 3 Days of Culture | 30.2 | B | 7.6 | 18.6 | B | 7.7 | 10.2 | A | 7.4 | 11.1 | A | 7.7 | 10.8 | A | 7.6 |
| After 5 Days of Culture | 38.7 | B | 7.4 | 33.1 | B | 7.8 | 20.7 | B | 7.6 | 19.1 | B | 7.6 | 16.4 | B | 7.6 |

TABLE 2-2-5

Example product 33
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 19.3 | B | 7.7 | 8.7 | A | 7.6 | 5.3 | A | 7.4 | 4.8 | A | 7.3 | 3.5 | A | 7.2 |
| After 2 Days of Culture | 22.7 | B | 7.8 | 20.6 | B | 7.3 | 10.4 | A | 7.1 | 9.8 | A | 7.5 | 6.6 | A | 7.3 |
| After 3 Days of Culture | 28.6 | B | 7.6 | 25.4 | B | 7.4 | 18.8 | B | 7.6 | 14.9 | B | 7.4 | 12.9 | B | 7.2 |
| After 5 Days of Culture | 38.4 | B | 7.8 | 34.8 | B | 7.5 | 20.5 | B | 7.4 | 22.6 | B | 7.8 | 24.5 | B | 7.5 |

*$\text{Log}_{10}\text{CFU/mL}$

TABLE 2-3-1

Example product 35
Concentration of Component (A)

| | 5 ppm | | | 10 ppm | | | 50 ppm | | | 100 ppm | | | 500 ppm | | |
|---|---|---|---|---|---|---|---|---|---|---|---|---|---|---|---|
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.1 | A | 7.6 | 2.1 | A | 7.9 | 1.9 | A | 7.8 | 2.0 | A | 7.5 | 1.7 | A | 7.9 |
| After 2 Days of Culture | 5.9 | A | 7.8 | 3.6 | A | 7.8 | 3.3 | A | 7.8 | 3.6 | A | 7.7 | 3.2 | A | 7.7 |
| After 3 Days of Culture | 30.1 | B | 7.7 | 9.9 | A | 7.8 | 5.3 | A | 7.7 | 5.8 | A | 7.6 | 4.7 | A | 7.8 |
| After 5 Days of Culture | 34.8 | B | 7.7 | 30.5 | B | 7.7 | 10.8 | A | 7.7 | 7.3 | A | 7.7 | 5.2 | A | 7.6 |

TABLE 2-3-2

| | Example product 38 Concentration of Component (A) | | | | | | | | | | | | | | | |
|---|---|---|---|---|---|---|---|---|---|---|---|---|---|---|---|---|
| | 5 ppm | | | 10 ppm | | | 50 ppm | | | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 3.2 | A | 7.4 | 1.9 | A | 7.2 | 1.6 | A | 7.5 | 1.9 | A | 7.5 | 1.6 | A | 7.4 |
| After 2 Days of Culture | 6.5 | A | 7.5 | 3.9 | A | 7.2 | 3.0 | A | 7.9 | 3.3 | A | 7.4 | 3.3 | A | 7.3 |
| After 3 Days of Culture | 25.8 | B | 7.5 | 10.7 | A | 7.4 | 6.5 | A | 7.8 | 5.2 | A | 7.5 | 4.9 | A | 7.4 |
| After 5 Days of Culture | 35.1 | B | 7.8 | 33.2 | B | 7.5 | 11.8 | B | 7.7 | 10.6 | A | 7.9 | 8.5 | A | 7.4 |

TABLE 2-3-3

| | Example product 42 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 3.1 | A | 7.8 | 2.0 | A | 7.3 | 1.9 | A | 7.6 |
| After 2 Days of Culture | 8.2 | A | 7.8 | 3.5 | A | 7.5 | 3.5 | A | 7.8 |
| After 3 Days of Culture | 26.1 | B | 7.7 | 11.0 | A | 7.6 | 6.7 | A | 7.6 |
| After 5 Days of Culture | 37.6 | B | 7.7 | 30.8 | B | 7.5 | 11.5 | B | 7.5 |

| | Example product 42 Concentration of Component (A) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.5 | A | 7.1 | 1.8 | A | 7.6 |
| After 2 Days of Culture | 3.2 | A | 7.5 | 2.9 | A | 7.6 |
| After 3 Days of Culture | 5.4 | A | 7.4 | 4.6 | A | 7.5 |
| After 5 Days of Culture | 10.3 | A | 7.3 | 8.2 | A | 7.3 |

TABLE 2-4-1

| | Comparative Product 3 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 28.5 | B | 8.1 | 27.3 | B | 7.6 | 25.3 | B | 7.9 |
| After 2 Days of Culture | 43.6 | C | 7.6 | 42.9 | C | 8.3 | 49.7 | C | 8.2 |
| After 3 Days of Culture | 53.4 | C | 7.9 | 51.8 | C | 8.2 | 53.8 | C | 8.0 |
| After 5 Days of Culture | 63.1 | C | 8.3 | 60.8 | C | 8.3 | 63.4 | C | 7.9 |

| | Comparative Product 3 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 27.3 | B | 7.9 | 23.6 | B | 8.1 |
| After 2 Days of Culture | 48.6 | C | 8.5 | 45.7 | C | 8.2 |
| After 3 Days of Culture | 57.3 | C | 8.5 | 50.6 | C | 8.0 |
| After 5 Days of Culture | 61.7 | C | 8.4 | 57.1 | C | 7.9 |

TABLE 2-4-2

| | Comparative Product 11 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 22.3 | B | 8.1 | 29.4 | B | 7.8 | 24.2 | B | 7.7 |
| After 2 Days of Culture | 42.3 | C | 7.8 | 41.6 | C | 8.2 | 48.2 | C | 8.1 |
| After 3 Days of Culture | 56.1 | C | 8.1 | 53.4 | C | 8.2 | 52.9 | C | 8.3 |
| After 5 Days of Culture | 60.8 | C | 8.1 | 62.6 | C | 8.1 | 61.7 | C | 8.2 |

| | Comparative Product 11 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 23.4 | B | 7.8 | 21.7 | B | 8.2 |
| After 2 Days of Culture | 41.6 | C | 8.2 | 47.3 | C | 8.1 |
| After 3 Days of Culture | 53.4 | C | 8.4 | 52.4 | C | 8.0 |
| After 5 Days of Culture | 60.7 | C | 8.3 | 58.6 | C | 8.3 |

TABLE 2-4-3

| | Comparative Product 13 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 25.3 | B | 8.0 | 24.3 | B | 7.8 | 21.7 | B | 8.0 |
| After 2 Days of Culture | 48.7 | C | 8.0 | 49.0 | C | 8.2 | 48.5 | C | 8.2 |
| After 3 Days of Culture | 52.4 | C | 8.3 | 50.6 | C | 8.1 | 52.3 | C | 8.1 |
| After 5 Days of Culture | 61.4 | C | 8.1 | 61.6 | C | 8.3 | 60.4 | C | 8.0 |

| | Comparative Product 13 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 26.2 | B | 7.9 | 20.7 | B | 8.3 |
| After 2 Days of Culture | 42.8 | C | 8.1 | 41.7 | C | 8.1 |
| After 3 Days of Culture | 56.8 | C | 8.2 | 55.3 | C | 8.4 |
| After 5 Days of Culture | 64.5 | C | 8.3 | 63.7 | C | 8.5 |

TABLE 2-4-4

| | Comparative Product 18 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 31.3 | B | 7.6 | 34.2 | B | 7.9 | 35.2 | B | 8.2 |
| After 2 Days of Culture | 45.8 | C | 8.0 | 49.7 | C | 8.4 | 43.5 | C | 8.1 |
| After 3 Days of Culture | 60.1 | C | 8.2 | 58.1 | C | 8.4 | 57.6 | C | 8.3 |
| After 5 Days of Culture | 63.5 | C | 8.1 | 63.1 | C | 8.2 | 60.9 | C | 8.4 |

| | Comparative Product 18 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 25.4 | B | 8.0 | 26.1 | B | 8.2 |
| After 2 Days of Culture | 45.2 | C | 8.2 | 49.9 | C | 8.1 |
| After 3 Days of Culture | 56.8 | C | 8.3 | 56.4 | C | 8.3 |
| After 5 Days of Culture | 64.2 | C | 8.2 | 62.3 | C | 8.1 |

TABLE 2-4-5

| | Comparative Product 26 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 33.3 | B | 8.2 | 32.8 | B | 7.9 | 30.7 | B | 8.1 |
| After 2 Days of Culture | 44.6 | C | 8.1 | 47.3 | C | 7.8 | 46.7 | C | 8.2 |
| After 3 Days of Culture | 57.3 | C | 8.1 | 56.1 | C | 8.1 | 52.9 | C | 8.3 |
| After 5 Days of Culture | 62.1 | C | 8.3 | 67.3 | C | 8.0 | 63.4 | C | 8.1 |

| | Comparative Product 26 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 30.4 | B | 7.8 | 34.6 | B | 8.2 |
| After 2 Days of Culture | 49.5 | C | 8.1 | 50.2 | C | 8.3 |
| After 3 Days of Culture | 56.1 | C | 8.3 | 56.8 | C | 8.3 |
| After 5 Days of Culture | 63.8 | C | 8.5 | 64.0 | C | 8.3 |

*$Log_{10}CFU/mL$

Example 3

Test for Inhibition of Biofilm Formation in Silicone Tube

Pseudomonas (Psuedomonas aeruginosa NBRC 13275) and Klebsiella (Klebsiella pneumoniae ATCC13883) were precultured using soybean-casein digest agar [SCD Agar Medium; manufactured by Nihon Pharmaceutical Co., Ltd.] at 37 degrees Celsius for 24 hours. Example product 9, Example product 14 and Example Product 30 used in Example 1 and Comparative Product 3 and Comparative Product 26 were respectively diluted in 1 L of Mueller-Hinton Broth [manufactured by Nippon Becton Dickinson, Co., Ltd.] so that the concentration of the component (A) or component (A') was 25 ppm or 100 ppm. A loop of the bacterial colonies on the agar medium described above was inoculated into each of the dilutions, and the culture solution suspended with bacteria were circulated in a silicone tube (inner diameter 5 mm, outer diameter 7 mm) manufactured by ARAM CORPORATION at 30 degrees Celsius, using a Masterflex metering pump system (system model No. 7553-80, Head No. 7016-21) manufactured by Cole-Parmer Instrument Company). Furthermore, the circulation of the culture solution was performed at a flow rate of 50 to 60 mL/min. Also, as a control, a test section was simultaneously provided in which bacteria were inoculated in Mueller-Hinton Broth with no added drugs.

The biofilm formation inside the silicone tube was observed by visual evaluation, and at the same time, the number of bacterial cells in the culture solution was measured. The state of the biofilm formation was graded such that the state in which no biofilm was formed was graded A, the state in which biofilm formation was commenced, with slight coloration on the surface of the silicone tube, was graded B, and the state in which biofilm formation was obvious was graded C.

The results are presented in Table 3-1-1 to Table 3-2-3. Table 3-1-1 to Table 3-1-3 present the results obtained with Pseudomonas (Pseudomonas aeruginosa NBRC 13275), while Table 3-2-1 to Table 3-2-3 present the results obtained with Klebsiella (Klebsiella pneumoniae ATCC 13883).

TABLE 3-1-1

| | Control | | Example product 9 | | | | Example product 14 | | | |
|---|---|---|---|---|---|---|---|---|---|---|
| | | | \multicolumn{8}{c}{Concentration of Component (A)} |
| | — | | 25 ppm | | 100 ppm | | 25 ppm | | 100 ppm | |
| | State of Biofilm Formation | No. of Bacterial Cells* | State of Biofilm Formation | No. of Bacterial Cells* | State of Biofilm Formation | No. of Bacterial Cells* | State of Biofilm Formation | No. of Bacterial Cells* | State of Biofilm Formation | No. of Bacterial Cells* |
| After 1 Day of Culture | B | 7.9 | A | 7.3 | A | 7.1 | A | 7.1 | A | 7.3 |
| After 3 Days of Culture | C | 8.5 | A | 7.9 | A | 7.6 | A | 7.6 | A | 7.5 |
| After 5 Days of Culture | C | 8.7 | A | 7.8 | A | 7.9 | A | 7.9 | A | 7.6 |
| After 7 Days of Culture | C | 8.6 | B | 7.9 | A | 7.8 | B | 7.8 | A | 7.9 |
| After 14 Days of Culture | C | 8.3 | B | 7.6 | B | 7.8 | B | 7.8 | A | 7.7 |

*$Log_{10}$CFU/mL

TABLE 3-1-2

| | Example product 30 | | | |
|---|---|---|---|---|
| | 25 ppm | | 100 ppm | |
| Concentration of Component (A) | State of Biofilm Formation | No. of Bacterial Cells* | State of Biofilm Formation | No. of Bacterial Cells* |
| After 1 Day of Culture | A | 7.3 | A | 7.2 |
| After 3 Days of Culture | A | 7.8 | A | 7.5 |
| After 5 Days of Culture | A | 7.8 | A | 7.7 |
| After 7 Days of Culture | A | 7.7 | A | 7.6 |
| After 14 Days of Culture | A | 7.8 | A | 7.5 |

TABLE 3-1-3

| | Comparative Product 3 | | | | Comparative Product 26 | | | |
|---|---|---|---|---|---|---|---|---|
| | \multicolumn{8}{c}{Concentration of Component (A')} |
| | 25 ppm | | 100 ppm | | 25 ppm | | 100 ppm | |
| | State of Biofilm Formation | No. of Bacterial Cells* | State of Biofilm Formation | No. of Bacterial Cells* | State of Biofilm Formation | No. of Bacterial Cells* | State of Biofilm Formation | No. of Bacterial Cells* |
| After 1 Day of Culture | B | 7.7 | B | 7.7 | B | 7.8 | B | 7.8 |
| After 3 Days of Culture | C | 8.3 | C | 8.2 | C | 8.4 | C | 8.2 |
| After 5 Days of Culture | C | 8.5 | C | 8.7 | C | 8.5 | C | 8.4 |
| After 7 Days of Culture | C | 8.5 | C | 8.4 | C | 8.4 | C | 8.8 |
| After 14 Days of Culture | C | 8.6 | C | 8.5 | C | 8.4 | C | 8.7 |

*$Log_{10}$CFU/mL

TABLE 3-2-1

| | Control | | Example product 9 Concentration of Component (A) | | | | Example product 14 | | | |
|---|---|---|---|---|---|---|---|---|---|---|
| | — | | 25 ppm | | 100 ppm | | 25 ppm | | 100 ppm | |
| | State of Biofilm Formation | No. of Bacterial Cells* | State of Biofilm Formation | No. of Bacterial Cells* | State of Biofilm Formation | No. of Bacterial Cells* | State of Biofilm Formation | No. of Bacterial Cells* | State of Biofilm Formation | No. of Bacterial Cells* |
| After 1 Day of Culture | B | 8.2 | A | 7.6 | A | 7.5 | A | 7.9 | A | 7.7 |
| After 3 Days of Culture | C | 8.9 | A | 8.0 | A | 7.9 | A | 7.8 | A | 7.9 |
| After 5 Days of Culture | C | 8.6 | A | 8.1 | A | 8.1 | A | 8.0 | A | 7.9 |
| After 7 Days of Culture | C | 8.8 | B | 8.0 | A | 8.3 | B | 8.1 | A | 8.2 |
| After 14 Days of Culture | C | 8.6 | B | 8.0 | A | 8.2 | B | 8.2 | A | 8.0 |

*Klebsiella pneumoniae* ATCC13883

TABLE 3-2-2

*Klebsiella pneumoniae* ATCC13883

| | Example product 30 Concentration of Component (A) | | | |
|---|---|---|---|---|
| | 25 ppm | | 100 ppm | |
| | State of Biofilm Formation | No. of Bacterial Cells* | State of Biofilm Formation | No. of Bacterial Cells* |
| After 1 Day of Culture | A | 7.6 | A | 7.8 |
| After 3 Days of Culture | A | 7.8 | A | 7.8 |
| After 5 Days of Culture | A | 7.9 | A | 7.9 |
| After 7 Days of Culture | A | 8.2 | A | 7.8 |
| After 14 Days of Culture | A | 8.1 | A | 7.9 |

TABLE 3-2-3

| | Comparative Product 3 | | | | Comparative Product 26 | | | |
|---|---|---|---|---|---|---|---|---|
| | Concentration of Component (A') | | | | | | | |
| | 25 ppm | | 100 ppm | | 25 ppm | | 100 ppm | |
| | State of Biofilm Formation | No. of Bacterial Cells* | State of Biofilm Formation | No. of Bacterial Cells* | State of Biofilm Formation | No. of Bacterial Cells* | State of Biofilm Formation | No. of Bacterial Cells* |
| After 1 Day of Culture | B | 7.9 | B | 7.8 | B | 8.0 | B | 7.9 |
| After 3 Days of Culture | C | 8.1 | C | 8.1 | C | 8.5 | C | 8.1 |
| After 5 Days of Culture | C | 8.6 | C | 8.1 | C | 8.3 | C | 8.3 |
| After 7 Days of Culture | C | 8.4 | C | 8.3 | C | 8.4 | C | 8.2 |
| After 14 Days of Culture | C | 8.5 | C | 8.1 | C | 8.5 | C | 8.2 |

*$Log_{10}CFU/mL$

In the case of using the products according to the present invention, it was confirmed that biofilm formation in silicone tubes could be remarkably inhibited. With regard to the measurement of the number of bacterial cells in the culture solutions tested simultaneously, the control, the example products, and the comparative products all resulted in bacterial growth. Thus, it is suggested that the biofilm formation is inhibited not by bactericidal or antimicrobial action.

Example 4

Verification for Ability to Inhibit Biofilm Formation and Bactericidal Power by Combinations of Alcohol or Adduct of Alcohol and Ethylene Oxide, and Surfactant Using the compounds (A-2), (A-3) and (A-7) as the component (A), and the compounds (B-1), (B-5), (B-11) and (B-12) as the component (B), the composition of Example products 47 to 54 and Comparative Products 31 to 34 as indicated in Table 4 were prepared.

*Pseudomonas* (*Pseudomonas aeruginosa* NBRC 13275) was pre-cultured using soybean-casein digest agar [SCD Agar Medium; manufactured by Nihon Pharmaceutical Co., Ltd.] at 37 degrees Celsius for 24 hours. The colonies grown on the medium were scraped off and suspended in 10 mM sterile phosphate buffer (pH 7.2). The resultant suspension was washed by centrifuging twice at 5,000×g for 15 minutes at 10 degrees Celsius, and then suspended again in 10 mM sterile phosphate buffer (pH 7.2) to prepare a bacterial suspension in which the bacterial concentration was adjusted to 1.0 as the absorbance at 600 nm ($OD_{600}$=1.0). Thereafter, 99 mL of Mueller-Hinton Broth [manufactured by Nippon Becton Dickinson, Co., Ltd.] was introduced into a 200-mL sterile screw cup [manufactured by EIKENKIZAI CO., LTD.], and at the same time, 1 mL each of the prepared biofilm formation inhibitor compositions was introduced thereto, the content of the cup being thoroughly mixed. The concentration of the component (A) was adjusted to 150 ppm, and then 0.1 mL of the bacterial suspension prepared as described above was inoculated thereinto.

Component (A)

(A-2) C10 alcohol [KALCOL 1098, manufactured by Kao Corporation]

(A-3) C12 alcohol [KALCOL 2098. manufactured by Kao Corporation]

(A-7) Adduct of C12 alcohol and 3 moles of ethylene oxide (NIKKOL BL-3SY, manufactured by Nikko Chemicals, Ltd., R'=C12 alkyl, p=3)

Component (B) surfactant [the number within the parentheses represents the average number of added moles of ethylene oxide]

(B-1) Sodium lauryl sulfate [EMAL 0, manufactured by Kao Corporation]

(B-5) Polyoxyethylene (12) lauryl ether [EMULGEN 120, manufactured by Kao Corporation]

(B-11) Polyoxyethylene (10) oleic acid ester [EMANON 4110, manufactured by Kao Corporation]

(B-12) Polyoxyethylene (25) hydrogenated castor oil [EMANON CH25, manufactured by Kao Corporation]

Using these culture solutions, static culture was initiated at 37 degrees Celsius. Immediately after, and at the designated time points of 3 hours and 24 hours after the contact with the biofilm formation inhibitor, the number of the bacterial cells in each of the culture solutions was measured, and at 12 hours and 24 hours after the initiation of culture, each of the culture solutions was centrifuged at 10,000×g for 30 minutes at 5 degrees Celsius. The precipitate was removed, dried in a vacuum desiccator for 24 hours, and weighed, with the weight thus measured being taken as the weight of the biofilm produced in the culture solution.

The results are presented in Table 4.

TABLE 4

| | | | | Example product 47 | Example product 48 | Example product 49 | Example product 50 | Example product 51 | Example product 52 |
|---|---|---|---|---|---|---|---|---|---|
| Inhibitor Composition | Blended Components (wt %) | (A) | A-2 | 1.5 | 1.5 | | | 1.5 | |
| | | | A-3 | | | 1.5 | 1.5 | | 1.5 |
| | | | A-7 | | | | | | |
| | | (B) | B-1 | | 9 | | 1.5 | | 0.8 |
| | | | B-5 | 4.5 | | 4.5 | | 1.0 | |
| | | | B-11 | | | | | | |
| | | | B-12 | | 9.0 | | 1.5 | | 0.8 |
| | | | Ion-Exchanged Water | Balance | Balance | Balance | Balance | Balance | Balance |
| | | | Total | 100 | 100 | 100 | 100 | 100 | 100 |
| | (A)/(B) | | | 1/3 | 1/6 | 1/3 | 1/1 | 1.5/1 | 1.9/1 |
| No. of Bacterial Cells* | Immediately After Contact | *P. aeruginosa* | | 8.08 | 8.08 | 8.08 | 8.08 | 8.08 | 8.08 |
| | | *K. pneumoniae* | | 8.18 | 8.18 | 8.18 | 8.18 | 8.18 | 8.18 |
| | After 3 Hours | *P. aeruginosa* | | 8.23 | 7.51 | 8.16 | 7.6 | 8.13 | 7.79 |
| | | *K. pneumoniae* | | 8.26 | 7.39 | 8.3 | 7.81 | 8.24 | 8.02 |
| | After 24 Hours | *P. aeruginosa* | | 8.67 | 8.35 | 8.2 | 8.52 | 8.71 | 8.53 |
| | | *K. pneumoniae* | | 9.12 | 8.64 | 9.03 | 8.47 | 9.01 | 8.97 |
| Amount of Biofilm (mg) | After 12 Hours | *P. aeruginosa* | | 5.5 | 4.7 | 5.6 | 4.4 | 7.1 | 5.8 |
| | | *K. pneumoniae* | | 3.4 | 3.0 | 3.4 | 2.8 | 6.8 | 9.3 |
| | After 24 Hours | *P. aeruginosa* | | 7.1 | 5.2 | 6.1 | 4.8 | 10.5 | 13.9 |
| | | *K. pneumoniae* | | 6.3 | 6.3 | 4.2 | 5.1 | 16.3 | 17.2 |

| | | | | Example product 53 | Example product 54 | Comp. product 31 | Comp. product 32 | Comp. product 33 | Comp. product 34 |
|---|---|---|---|---|---|---|---|---|---|
| Inhibitor Composition | Blended Components (wt %) | (A) | A-2 | | | | | 1.5 | |
| | | | A-3 | | | | | | |
| | | | A-7 | 1.5 | 1.5 | | | | |

TABLE 4-continued

|  |  | (B) | B-1 |  |  |  |  |  | 9 |
|---|---|---|---|---|---|---|---|---|---|
|  |  |  | B-5 | 10.0 |  |  | 4.5 |  |  |
|  |  |  | B-11 |  | 1.5 |  |  | 0.305 |  |
|  |  |  | B-12 |  |  |  |  | 0.305 |  |
|  |  |  | Ion-Exchanged Water | Balance | Balance | Balance | Balance | Balance | Balance |
|  |  |  | Total | 100 | 100 | 100 | 100 | 100 | 100 |
|  | (A)/(B) |  |  | 1/6.7 | 1/1 | — | — | 2.5/1 | — |
| No. of Bacterial Cells* | Immediately After Contact | P. aeruginosa |  | 8.08 | 8.08 | 8.08 | 8.08 | 8.08 | 8.08 |
|  |  | K. pneumoniae |  | 8.18 | 8.18 | 8.18 | 8.18 | 8.18 | 8.18 |
|  | After 3 Hours | P. aeruginosa |  | 7.86 | 8.09 | 8.4 | 8.36 | 5.72 | 7.42 |
|  |  | K. pneumoniae |  | 8.03 | 8.16 | 8.38 | 8.41 | 4.58 | 7.58 |
|  | After 24 Hours | P. aeruginosa |  | 7.76 | 8.21 | 9.11 | 9.03 | 8.32 | 8.86 |
|  |  | K. pneumoniae |  | 8.32 | 8.59 | 9.73 | 9.74 | 8.92 | 9.43 |
| Amount of Biofilm (mg) | After 12 Hours | P. aeruginosa |  | 4.9 | 6.8 | 20.6 | 18.2 | 10.1 | 12.5 |
|  |  | K. pneumoniae |  | 3.8 | 8.7 | 13.8 | 13.4 | 9.2 | 11.3 |
|  | After 24 Hours | P. aeruginosa |  | 6.2 | 11.2 | 68.1 | 57.2 | 68.9 | 53.7 |
|  |  | K. pneumoniae |  | 6.7 | 13.8 | 50.3 | 43.1 | 43.3 | 46.1 |

*$Log_{10}CFU/mL$

As indicated in Table 4, it was found that when the ratio of the component (A) and the component (B) is set at 2 or less, and preferably 1/1 to 1/10, the effect of inhibiting biofilm formation on a long-term basis is manifested (Example products 47 to 54), but the composition having less amount of the component (B) (the ratio (A)/(B) is 2.5, Comparative Product 33) or the composition having only the component (B) (Comparative Product 32, Comparative Product 34) do not exhibit any biofilm formation inhibitory effect.

It also appeared that there was no correlation between the bactericidal effect and the biofilm formation inhibitory effect.

(2) Examples Using Compounds Represented by Formula (2)

Example 5

Blending of Biofilm Formation Inhibitor Composition, and Verification of Capability to Inhibit Biofilm Formation Component (A) [Formula (2): EO represents an ethyleneoxy group, and m and n each represent the average number of added moles]

Chem. 5

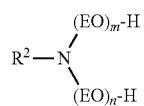

(A-21) C8 amine [FARMIN 08D, manufactured by Kao Corporation, $R^2$=C8 alkyl, m+n=0]
(A-22) C10 amine [decylamine, manufactured by Wako Pure Chemical Industries, Ltd., $R^2$=C10 alkyl, m+n=0]
(A-23) C12 amine [FARMIN 20D, manufactured by Kao Corporation, $R^2$=C12 alkyl, m+n=0]
(A-24) C12 amine hydrochloride [dodecylamine hydrochloride, manufactured by Wako Pure Chemical Industries, Ltd., $R^2$=C12 alkyl, m+n=0]
(A-25) Cocoamine [FARMIN CS, manufactured by Kao Corporation, $R^2$=C8-14 alkyl (coconut composition), m+n=0]
(A-26) Cocoamine acetate [ACETAMIN 24, manufactured by Kao Corporation, $R^2$=C8-14 alkyl (coconut composition), m+n=0]
(A-27) Adduct of cocoamine and 2 moles of ethylene oxide [AMIET 102, manufactured by Kao Corporation, $R^2$=C8-14 alkyl (coconut composition), m+n=2]
(A-28) Adduct of cocoamine and 5 moles of ethylene oxide [AMIET 105, manufactured by Kao Corporation, $R^2$=C8-14 alkyl (coconut composition), m+n=5]

Component (A') [Formula (2): EO represents an ethyleneoxy group, and m and n each represent the average number of added moles]

Chem. 6

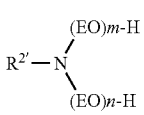

(A'-21) C3 amine [propylamine, manufactured by Wako Pure Chemical Industries, Ltd., $R^{2'}$=C3 alkyl, m+n=0]
(A'-22) C3 amine hydrochloride [propylamine hydrochloride, manufactured by Wako Pure Chemical Industries, Ltd., $R^{2'}$=C3 alkyl, m+n=0]
(A'-23) C6 amine [hexylamine, manufactured by Wako Pure Chemical Industries, Ltd., $R^{2'}$=C6 alkyl, m+n=0]
(A'-24) C6 amine hydrochloride [hexylamine hydrochloride, manufactured by Wako Pure Chemical Industries, Ltd., $R^{2'}$=C6 alkyl, m+n=0]
(A'-25) Hydrogenated tallow amine [FARMIN 86T, manufactured by Kao Corporation, $R^{2'}$=C16, C18 alkyl, m+n=0]
(A'-26) C18 amine [FARMIN 80V, manufactured by Kao Corporation, $R^{2'}$=C18 alkyl, m+n=0]
(A'-27) Oleylamine [FARMIN 0, manufactured by Kao Corporation, $R^{2'}$=C18 alkenyl, m+n=0]
(A'-28) Adduct of hydrogenated tallow amine and 2 moles of ethylene oxide [AMIET 302, manufactured by Kao Corporation, $R^{2'}$=C16, C18 alkyl, m+n=2]
(A'-29) Adduct of hydrogenated tallow amine and 20 moles of ethylene oxide [AMIET 320, manufactured by Kao Corporation, $R^{2'}$=C16, C18 alkyl, m+n=20]

Component (B) surfactant [the number within the parentheses represents the average number of added moles of ethylene oxide]

<Anionic Surfactants>

(B-1) Sodium lauryl sulfate [EMAL 0, manufactured by Kao Corporation] (B-2) Sodium polyoxyethylene (2) lauryl ether sulfate [EMAL 20C, manufactured by Kao Corporation; active ingredient 25% by weight]

(B-3) Sodium polyoxyethylene (4.5) lauryl ether acetate [KAO AKYPO RLM45-NV, manufactured by Kao Corporation; active ingredient 24% by weight]

<Nonionic Surfactants>

(B-4) Polyoxyethylene (6) lauryl ether [EMULGEN 106, manufactured by Kao Corporation]

(B-5) Polyoxyethylene (12) lauryl ether [EMULGEN 120, manufactured by Kao Corporation]

(B-6) Lauryl glucoside [MYDOL 12, manufactured by Kao Corporation]

(B-7) Decyl glycerin monocaprylate [SY-GLYSTER MCA750, manufactured by SAKAMOTO YAKUHIN KOGYO CO., LTD.]

(B-8) Sorbitan monolaurate [RHEODOLSP-L10, manufactured by Kao Corporation]

(B-9) Polyoxyethylene (6) sorbitan monolaurate [RHEODOL TW-L106, manufactured by Kao Corporation]

(B-10) Polyoxyethylene (20) sorbitan monolaurate [RHEODOL TW-L120, manufactured by Kao Corporation]

Active ingredients were blended on a weight basis such that the concentration of the component (A) or component (A') was fixed at 1% by weight, while the concentration of the component (B) was selected from 1% by weight, 3% by weight, 6% by weight and 10% by weight, with the balance being ion-exchanged water. The blend was diluted using Mueller-Hinton Broth [manufactured by Nippon Becton Dickinson Co., Ltd.] to a concentration of 100 ppm of the component (A) or component (A'). The dilution was taken in an amount of 2 mL and placed on a 24-well microplate [manufactured by ASAHI TECHNO GLASS CORPORATION].

*Pseudomonas* (*Pseudomonas aeruginosa* NBRC 13275), *Serratia* (*Serratia marcescens* NBRC 12648), and *Klebsiella* (*Klebsiella pneumoniae* ATCC 13883) were each pre-cultured at 37 degrees Celsius for 24 hours using soybean-casein digest agar [SCD Agar Medium; manufactured by Nihon Pharmaceutical Co., Ltd.], to form colonies. A very small amount of bacterial clusters from the colonies formed was inoculated into each of the above-described test solutions on the microplate, using a sterilized bamboo skewer. The inoculated solution was incubated at 37 degrees Celsius for 48 hours, then the culture solution was discarded, and the state of formation of the biofilm adhering on the microplate wall was observed by visual evaluation. The state of the biofilm was graded such that the state in which the biofilm covered 0 to less than 20% of the microplate wall surface was graded A; the state in which the biofilm covered 20% or more to less than 40% of the wall surface was graded B; the state in which the biofilm covered 40% or more to less than 60% of the wall surface was graded C; and the state in which the biofilm covered 60% or more of the wall surface was graded D. The results are presented in Table 5-1 to Table 5-4.

TABLE 5-1

| | Example product 55 | Example product 56 | Example product 57 | Example product 58 | Example product 59 | Example product 60 | Example product 61 | Example product 62 |
|---|---|---|---|---|---|---|---|---|
| Component (A) | | | | | | | | |
| A-21 | 1.0 | 1.0 | 1.0 | | | | | |
| A-22 | | | | 1.0 | 1.0 | 1.0 | 1.0 | 1.0 |
| A-23 | | | | | | | | |
| A-24 | | | | | | | | |
| Surfactant (B) [Anionic Surfactant] | | | | | | | | |
| B-1 | 3.0 | | | 3.0 | | | | |
| B-2 | | | | | | | | |
| B-3 | | | | | | | | |
| [Nonionic Surfactant] | | | | | | | | |
| B-4 | | | | | 3.0 | | | |
| B-5 | | 3.0 | | | | 6.0 | | |
| B-6 | | | | | | | 3.0 | |
| B-7 | | | | | | | | |
| B-8 | | | | | | | | |
| B-9 | | | | | | | | 6.0 |
| B-10 | | | 3.0 | | | | | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition | | | | | | | | |
| *P. aeruginosa* | B | B | B | B | A | A | A | A |
| *S. marcescens* | B | B | B | B | A | A | A | A |
| *K. pneumoniae* | B | B | B | B | A | A | A | A |

TABLE 5-1-continued

|  | Example product 63 | Example product 64 | Example product 65 | Example product 66 | Example product 67 | Example product 68 | Example product 69 | Example product 70 |
|---|---|---|---|---|---|---|---|---|
| Component (A) | | | | | | | | |
| A-21 | | | | | | | | |
| A-22 | | | | | | | | |
| A-23 | 1.0 | 1.0 | 1.0 | 1.0 | 1.0 | | | |
| A-24 | | | | | | 1.0 | 1.0 | 1.0 |
| Surfactant (B) [Anionic Surfactant] | | | | | | | | |
| B-1 | | | | | | | | |
| B-2 | 3.0 | | | | | | | |
| B-3 | | | | | | 3.0 | | |
| [Nonionic Surfactant] | | | | | | | | |
| B-4 | | 6.0 | | | | | | |
| B-5 | | | 3.0 | | | | 6.0 | |
| B-6 | | | | | | | | |
| B-7 | | | | 3.0 | | | | |
| B-8 | | | | | | | | 3.0 |
| B-9 | | | | | | | | |
| B-10 | | | | | 3.0 | | | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition | | | | | | | | |
| *P. aeruginosa* | B | A | A | A | A | B | A | A |
| *S. marcescens* | B | A | A | A | A | B | A | A |
| *K. pneumoniae* | B | A | A | A | A | B | A | A |

TABLE 5-2

|  | Example product 71 | Example product 72 | Example product 73 | Example product 74 | Example product 75 | Example product 76 | Example product 77 | Example product 78 |
|---|---|---|---|---|---|---|---|---|
| Component (A) | | | | | | | | |
| A-25 | 1.0 | 1.0 | 1.0 | 1.0 | 1.0 | | | |
| A-26 | | | | | | 1.0 | 1.0 | 1.0 |
| A-27 | | | | | | | | |
| A-28 | | | | | | | | |
| Surfactant (B) [Anionic Surfactant] | | | | | | | | |
| B-1 | 6.0 | | | | | | | |
| B-2 | | | | | | 3.0 | | |
| B-3 | | | | | | | | |
| [Nonionic Surfactant] | | | | | | | | |
| B-4 | | 6.0 | | | | | | |
| B-5 | | | 3.0 | | | | 6.0 | |
| B-6 | | | | | | | | 3.0 |
| B-7 | | | | 3.0 | | | | |
| B-8 | | | | | | | | |
| B-9 | | | | | | | | |
| B-10 | | | | | 3.0 | | | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |

TABLE 5-2-continued

| State of Biofilm Inhibition | | | | | | | | |
|---|---|---|---|---|---|---|---|---|
| P. aeruginosa | B | A | A | A | A | B | A | A |
| S. marcescens | B | A | A | A | A | B | A | A |
| K. pneumoniae | B | A | A | A | A | B | A | A |

|  | Example product 79 | Example product 80 | Example product 81 | Example product 82 | Example product 83 | Example product 84 | Example product 85 | Example product 86 |
|---|---|---|---|---|---|---|---|---|
| Component (A) | | | | | | | | |
| A-25 | | | | | | | | |
| A-26 | 1.0 | | | | | | | |
| A-27 | | 1.0 | 1.0 | 1.0 | 1.0 | | | |
| A-28 | | | | | | 1.0 | 1.0 | 1.0 |
| Surfactant (B) [Anionic Surfactant] | | | | | | | | |
| B-1 | | | | | | | | |
| B-2 | | | | | | 3.0 | | |
| B-3 | | 6.0 | | | | | | |
| [Nonionic Surfactant] | | | | | | | | |
| B-4 | | | 3.0 | | | | | |
| B-5 | | | | | | | 3.0 | |
| B-6 | | | | | | | | |
| B-7 | | | | | | | | 3.0 |
| B-8 | | | | 3.0 | | | | |
| B-9 | 3.0 | | | | | | | |
| B-10 | | | | | 3.0 | | | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition | | | | | | | | |
| P. aeruginosa | A | B | A | A | A | B | B | B |
| S. marcescens | A | B | A | A | A | B | B | B |
| K. pneumoniae | A | B | A | A | A | B | B | B |

TABLE 5-3

|  | Comparative Product 35 | Comparative Product 36 | Comparative Product 37 | Comparative Product 38 | Comparative Product 39 | Comparative Product 40 | Comparative Product 41 | Comparative Product 42 |
|---|---|---|---|---|---|---|---|---|
| Component (A') | | | | | | | | |
| A'-21 | 1.0 | 1.0 | 1.0 | | | | | |
| A'-22 | | | | 1.0 | 1.0 | 1.0 | | |
| A'-23 | | | | | | | 1.0 | 1.0 |
| A'-24 | | | | | | | | |
| A'-25 | | | | | | | | |
| Surfactant (B) [Anionic Surfactant] | | | | | | | | |
| B-1 | 3.0 | | | | | | | |
| B-2 | | | | 3.0 | | | 6.0 | |
| B-3 | | | | | | | | |
| [Nonionic Surfactant] | | | | | | | | |
| B-4 | | | | | | | | |
| B-5 | | 3.0 | | | | | | |

TABLE 5-3-continued

|  | | | | | | | | |
|---|---|---|---|---|---|---|---|---|
| B-6 | | | | | 6.0 | | | |
| B-7 | | 3.0 | | | | | | |
| B-8 | | | | | | | | 3.0 |
| B-9 | | | | | | | | |
| B-10 | | | | | | 3.0 | | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition | | | | | | | | |
| *P. aeruginosa* | D | D | D | D | D | D | D | D |
| *S. marcescens* | D | D | D | D | D | D | D | D |
| *K. pneumoniae* | D | D | D | D | D | D | D | D |

|  | Comparative Product 43 | Comparative Product 44 | Comparative Product 45 | Comparative Product 46 | Comparative Product 47 | Comparative Product 48 | Comparative Product 49 |
|---|---|---|---|---|---|---|---|
| Component (A') | | | | | | | |
| A□-21 | | | | | | | |
| A□-22 | | | | | | | |
| A□-23 | 1.0 | | | | | | |
| A□-24 | | 1.0 | 1.0 | 1.0 | | | |
| A□-25 | | | | | 1.0 | 1.0 | 1.0 |
| Surfactant (B) [Anionic Surfactant] | | | | | | | |
| B-1 | | | | | 3.0 | | |
| B-2 | | | | | | | |
| B-3 | | 6.0 | | | | | |
| [Nonionic Surfactant] | | | | | | | |
| B-4 | | | | | | | |
| B-5 | | | 6.0 | | | 3.0 | |
| B-6 | | | | | | | |
| B-7 | | | | 3.0 | | | |
| B-8 | | | | | | | |
| B-9 | 3.0 | | | | | | |
| B-10 | | | | | | | 3.0 |
| Ion-Exchanged Water | Balance | Balance | Balance | Balance | Balance | Balance | Balance |
| Total | 100.0 | 100.0 | 100.0 | 100.0 | 100.0 | 100.0 | 100.0 |
| State of Biofilm Inhibition | | | | | | | |
| *P. aeruginosa* | D | D | D | D | D | D | D |
| *S. marcescens* | D | D | D | D | D | D | D |
| *K. pneumoniae* | D | D | D | D | D | D | D |

TABLE 5-4

|  | Comparative Product 50 | Comparative Product 51 | Comparative Product 52 | Comparative Product 53 | Comparative Product 54 | Comparative Product 55 |
|---|---|---|---|---|---|---|
| Component (A') | | | | | | |
| A□-26 | 1.0 | 1.0 | 1.0 | | | |
| A□-27 | | | | 1.0 | 1.0 | 1.0 |
| A□-28 | | | | | | |
| A□-29 | | | | | | |
| Surfactant (B) [Anionic Surfactant] | | | | | | |
| B-1 | 3.0 | | | | | |
| B-2 | | | | | | |
| B-3 | | | | 3.0 | | |

TABLE 5-4-continued

| | | | | | | |
|---|---|---|---|---|---|---|
| [Nonionic Surfactant] | | | | | | |
| B-4 | | | | | | |
| B-5 | | 3.0 | | | | |
| B-6 | | | | | 6.0 | |
| B-7 | | | | | | |
| B-8 | | | | | | 3.0 |
| B-9 | | | 3.0 | | | |
| B-10 | | | | | | |
| Ion-Exchanged Water | Balance | Balance | Balance | Balance | Balance | Balance |
| Total | 100.0 | 100.0 | 100.0 | 100.0 | 100.0 | 100.0 |
| State of Biofilm Inhibition | | | | | | |
| P. aeruginosa | D | D | D | D | D | D |
| S. marcescens | D | D | D | D | D | D |
| K. pneumoniae | D | D | D | D | D | D |

| | Comparative Product 56 | Comparative Product 57 | Comparative Product 58 | Comparative Product 59 | Comparative Product 60 | Comparative Product 61 |
|---|---|---|---|---|---|---|
| Component (A') | | | | | | |
| A□-26 | | | | | | |
| A□-27 | | | | | | |
| A□-28 | 1.0 | 1.0 | 1.0 | | | |
| A□-29 | | | | 1.0 | 1.0 | 1.0 |
| Surfactant (B) | | | | | | |
| [Anionic Surfactant] | | | | | | |
| B-1 | | | | 3.0 | | |
| B-2 | 3.0 | | | | | |
| B-3 | | | | | | |
| [Nonionic Surfactant] | | | | | | |
| B-4 | | | | | | |
| B-5 | | | | | 6.0 | |
| B-6 | | | | | | |
| B-7 | | 3.0 | | | | |
| B-8 | | | | | | |
| B-9 | | | | | | 3.0 |
| B-10 | | | 3.0 | | | |
| Ion-Exchanged Water | Balance | Balance | Balance | Balance | Balance | Balance |
| Total | 100.0 | 100.0 | 100.0 | 100.0 | 100.0 | 100.0 |
| State of Biofilm Inhibition | | | | | | |
| P. aeruginosa | D | D | D | D | D | D |
| S. marcescens | D | D | D | D | D | D |
| K. pneumoniae | D | D | D | D | D | D |

Example 6

Test for Reduction of Biofilm Production in Large Volume Plastic Cup

Pseudomonas (Pseudomonas aeruginosa NBRC 13275) was pre-cultured at 37 degrees Celsius for 24 hours, using soybean-casein digest agar [SCD Agar Medium; manufactured by Nihon Pharmaceutical Co., Ltd.]. The colonies formed on the medium were scraped off and suspended in 10 mM sterile phosphate buffer (pH 7.2), and then the suspension was washed by centrifuging twice at 5,000×g for 15 minutes at 10 degrees Celsius. The resultant precipitate was again suspended in 10 mM sterile phosphate buffer (pH 7.2) to prepare a bacterial suspension in which the bacterial concentration was adjusted to 1.0 as the absorbance at 600 nm ($OD_{600}$=1.0). Thereafter, 100 mL of Mueller-Hinton Broth [manufactured by Nippon Becton Dickinson Co., Ltd.] and each of the 15 species of the test drugs selected in Example 5 were introduced into a 200-mL sterilized screw cup [manufactured by EIKENKIZAI CO., LTD.], and thoroughly mixed. The concentration of the component (A) or component (A') was adjusted to 5 ppm, 10 ppm, 50 ppm, 100 ppm or 500 ppm, and then 0.1 mL of the bacterial suspension prepared as described above was inoculated thereinto. Furthermore, as a control, a test section was simultaneously provided in which the bacteria were inoculated as described above into Mueller-Hinton Broth with no added drugs.

These were statically cultured at 37 degrees Celsius. At the designated time points of 1 day, 2 days, 3 days and 5 days after the initiation of culture, the number of bacterial cells in the culture solution was measured, and the biofilm formed inside the cup was observed by visual evaluation. Subsequently, the culture solution was centrifuged at 10,000×g for 30 minutes at 5 degrees Celsius, and the precipitate was removed, dried in a vacuum desiccator for 24 hours, and weighed, with the weight thus measured being taken as the weight of the biofilm produced in the culture solution. Furthermore, the state of the biofilm formation was graded such that the state in which no biofilm was confirmed in the cup was graded A; the state in which the formation of a biofilm started inside the cup at the air-liquid interface was graded B; and the state in which a biofilm was formed to extend from the air-liquid interface down to the culture solution was graded C.

The results are presented in Table 6-1-1 to Table 6-3-5.

TABLE 6-1-1

| | Control | | | Example product 55 Concentration of Component (A) | | | | | |
|---|---|---|---|---|---|---|---|---|---|
| | — | | | 5 ppm | | | 10 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 32.4 | B | 8.0 | 19.8 | B | 7.8 | 20.1 | B | 8.0 |
| After 2 Days of Culture | 49.9 | C | 8.2 | 22.6 | B | 8.2 | 20.6 | B | 8.1 |
| After 3 Days of Culture | 51.3 | C | 8.4 | 24.1 | B | 8.3 | 29.0 | B | 8.2 |
| After 5 Days of Culture | 63.9 | C | 8.5 | 34.6 | B | 8.5 | 32.7 | B | 8.2 |

| | Example product 55 Concentration of Component (A) | | | | | | | | |
|---|---|---|---|---|---|---|---|---|---|
| | 50 ppm | | | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 11.6 | A | 7.9 | 13.2 | A | 8.0 | 12.3 | A | 8.0 |
| After 2 Days of Culture | 18.5 | B | 8.0 | 17.5 | B | 8.1 | 16.0 | B | 7.8 |
| After 3 Days of Culture | 24.3 | B | 8.0 | 20.3 | B | 8.2 | 21.7 | B | 7.9 |
| After 5 Days of Culture | 29.7 | B | 8.1 | 26.7 | B | 8.2 | 23.6 | B | 8.1 |

TABLE 6-1-2

| | Example product 59 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.8 | A | 7.7 | 1.9 | A | 7.9 | 1.8 | A | 7.9 |
| After 2 Days of Culture | 5.1 | A | 7.9 | 3.2 | A | 8.0 | 2.5 | A | 7.8 |
| After 3 Days of Culture | 22.0 | B | 7.8 | 9.4 | A | 8.0 | 4.6 | A | 7.9 |
| Alter 5 Days of Culture | 30.8 | B | 7.7 | 24.9 | B | 7.7 | 10.0 | A | 7.8 |

TABLE 6-1-2-continued

|  | | Example product 59 Conentration of Component (A) | | | | | |
|---|---|---|---|---|---|---|---|
|  | | 100 ppm | | | 500 ppm | | |
|  | | Amount of Biofilm (mg) | Visual Judgment of Biofilm | No. of Bacterial Cells* | Amount of Biofilm (mg) | Visual Judgment of Biofilm | No. of Bacterial Cells* |
|  | After 1 Day of Culture | 2.0 | A | 8.0 | 2.1 | A | 7.7 |
|  | After 2 Days of Culture | 2.5 | A | 7.9 | 3.1 | A | 7.8 |
|  | After 3 Days of Culture | 3.1 | A | 7.8 | 4.8 | A | 7.9 |
|  | Alter 5 Days of Culture | 7.5 | A | 7.7 | 7.1 | A | 7.5 |

TABLE 6-1-3

| | Example product 62 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 3.2 | A | 7.7 | 1.6 | A | 7.7 | 1.4 | A | 7.8 |
| After 2 Days of Culture | 5.2 | A | 7.6 | 2.8 | A | 7.9 | 3.9 | A | 7.6 |
| After 3 Days of Culture | 19.6 | B | 7.7 | 7.9 | A | 7.8 | 5.2 | A | 7.7 |
| After 5 Days of Culture | 31.4 | B | 8.0 | 26.8 | B | 7.9 | 16.4 | B | 7.4 |

|  | | Example product 62 Concentration of Component (A) | | | | | |
|---|---|---|---|---|---|---|---|
|  | | 100 ppm | | | 500 ppm | | |
|  | | Amount of Biofilm (mg) | Visual Judgment of Biofilm | No. of Bacterial Cells* | Amount of Biofilm (mg) | Visual Judgment of Biofilm | No. of Bacterial Cells* |
|  | After 1 Day of Culture | 2.2 | A | 7.6 | 1.6 | A | 7.5 |
|  | After 2 Days of Culture | 3.5 | A | 7.7 | 2.8 | A | 7.6 |
|  | After 3 Days of Culture | 4.0 | A | 7.9 | 4.6 | A | 7.5 |
|  | After 5 Days of Culture | 7.8 | A | 7.5 | 4.9 | A | 7.4 |

TABLE 6-1-4

| | Example product 65 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 3.0 | A | 7.5 | 1.7 | A | 7.8 | 2.7 | A | 7.7 |
| After 2 Days of Culture | 6.9 | A | 8.0 | 3.6 | A | 7.9 | 2.6 | A | 7.6 |

TABLE 6-1-4-continued

| | | | | | | | | |
|---|---|---|---|---|---|---|---|---|
| After 3 Days of Culture | 21.8 | B | 7.9 | 10.1 | A | 7.5 | 5.1 | A | 7.8 |
| After 5 Days of Culture | 40.1 | B | 7.8 | 32.7 | B | 7.8 | 8.9 | A | 7.9 |

| | Example product 65 Concentration of Component (A) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.6 | A | 7.4 | 2.1 | A | 7.5 |
| After 2 Days of Culture | 2.6 | A | 7.5 | 3.9 | A | 7.6 |
| After 3 Days of Culture | 5.7 | A | 7.7 | 4.7 | A | 7.8 |
| After 5 Days of Culture | 9.8 | A | 7.6 | 8.4 | A | 7.5 |

TABLE 6-1-5

| | Example product 70 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 3.8 | A | 7.7 | 2.9 | A | 7.6 | 1.9 | A | 7.7 |
| After 2 Days of Culture | 6.1 | A | 7.8 | 3.1 | A | 7.7 | 3.6 | A | 7.8 |
| After 3 Days of Culture | 25.3 | B | 7.7 | 11.6 | A | 7.6 | 5.9 | A | 7.6 |
| After 5 Days of Culture | 31.9 | B | 7.7 | 36.8 | B | 7.8 | 10.7 | B | 8 |

| | Example product 70 Concentration of Component (A) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 1.8 | A | 7.5 | 1.6 | A | 7.6 |
| After 2 Days of Culture | 3.7 | A | 7.6 | 3.9 | A | 7.7 |
| After 3 Days of Culture | 5.0 | A | 7.4 | 4.1 | A | 7.6 |
| After 5 Days of Culture | 6.8 | A | 7.8 | 5.7 | A | 7.8 |

*$\mathrm{Log}_{10}\mathrm{CFU/mL}$

TABLE 6-2-1

| | Example product 72 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.8 | A | 7.6 | 1.9 | A | 7.6 | 2.0 | A | 7.5 |
| After 2 Days of Culture | 7.5 | A | 7.7 | 2.7 | A | 7.4 | 3.8 | A | 7.6 |
| After 3 Days of Culture | 19.6 | B | 7.9 | 8.6 | A | 7.5 | 5.9 | A | 7.5 |
| After 5 Days of Culture | 32.1 | B | 7.6 | 26.5 | B | 7.6 | 9.9 | A | 7.9 |

| | Example product 72 Concentration of Component (A) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 1.8 | A | 7.3 | 2.0 | A | 7.6 |
| After 2 Days of Culture | 6.1 | A | 7.5 | 2.9 | A | 7.5 |
| After 3 Days of Culture | 5.9 | A | 7.4 | 4.2 | A | 7.6 |
| After 5 Days of Culture | 10.2 | A | 7.7 | 7.8 | A | 7.7 |

TABLE 6-2-2

| | Example product 74 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 4.2 | A | 7.5 | 2.3 | A | 7.5 | 1.8 | A | 7.6 |
| After 2 Days of Culture | 7.7 | A | 7.7 | 4.2 | A | 7.6 | 2.9 | A | 8.0 |
| After 3 Days of Culture | 19.8 | B | 7.5 | 10.2 | A | 7.9 | 7.5 | A | 7.9 |
| After 5 Days of Culture | 30.8 | B | 7.8 | 36.2 | B | 7.8 | 13.7 | B | 7.7 |

| | Example product 74 Concentration of Component (A) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.6 | A | 7.9 | 1.5 | A | 7.5 |
| After 2 Days of Culture | 3.8 | A | 7.4 | 2.7 | A | 7.4 |
| After 3 Days of Culture | 5.5 | A | 7.8 | 4.5 | A | 7.3 |
| After 5 Days of Culture | 9.9 | A | 7.8 | 7.6 | A | 7.5 |

TABLE 6-2-3

| | Example product 77 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 3.8 | A | 7.3 | 2.1 | A | 7.2 | 1.8 | A | 7.5 |
| After 2 Days of Culture | 6.8 | A | 7.3 | 7.9 | A | 7.4 | 2.7 | A | 7.7 |
| After 3 Days of Culture | 21.0 | B | 7.5 | 17.9 | B | 7.5 | 6.8 | A | 7.6 |
| After 5 Days of Culture | 28.5 | B | 7.6 | 20.7 | B | 7.3 | 17.6 | B | 7.8 |

| | Example product 77 Concentration of Component (A) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.0 | A | 7.6 | 1.5 | A | 7.1 |
| After 2 Days of Culture | 5.1 | A | 7.5 | 6.4 | A | 7.6 |
| After 3 Days of Culture | 7.6 | A | 7.8 | 8.4 | A | 7.4 |
| After 5 Days of Culture | 15.7 | B | 7.9 | 15.3 | B | 7.5 |

TABLE 6-2-4

| | Example product 82 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 20.4 | B | 8.0 | 11.8 | A | 7.9 | 8.9 | A | 7.8 |
| After 2 Days of Culture | 21.9 | B | 7.9 | 21.0 | B | 8.1 | 11.3 | A | 8.2 |
| After 3 Days of Culture | 28.3 | B | 7.9 | 23.6 | B | 8.0 | 22.2 | B | 8.3 |
| After 5 Days of Culture | 31.5 | B | 8.3 | 30.4 | B | 7.9 | 27.1 | B | 8.0 |

| | Example product 82 Concentration of Component (A) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 11.2 | A | 7.7 | 10.5 | A | 8.0 |
| After 2 Days of Culture | 15.1 | A | 7.9 | 12.6 | A | 8.1 |
| After 3 Days of Culture | 22.8 | B | 8.2 | 22.8 | B | 8.0 |
| After 5 Days of Culture | 30.0 | B | 8.1 | 27.4 | B | 7.9 |

TABLE 6-2-5

| | Example product 84 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 19.6 | B | 8.0 | 19.2 | B | 7.9 | 9.8 | A | 8.0 |
| After 2 Days of Culture | 20.7 | B | 8.2 | 23.1 | B | 7.9 | 16.4 | B | 8.0 |
| After 3 Days of Culture | 26.1 | B | 8.2 | 27.6 | B | 8.0 | 25.5 | B | 8.0 |
| After 5 Days of Culture | 32.1 | B | 8.4 | 30.5 | B | 8.1 | 30.2 | B | 8.3 |

| | Example product 84 Concentration of Component (A) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 10.6 | A | 8 | 9.9 | A | 8.0 |
| After 2 Days of Culture | 15.7 | B | 7.9 | 16.2 | B | 7.9 |
| After 3 Days of Culture | 24.1 | B | 8.0 | 18.5 | B | 8.0 |
| After 5 Days of Culture | 28.0 | B | 8.2 | 27.6 | B | 8.2 |

*$Log_{10}CFU/mL$

TABLE 6-3-1

| | Comparative product 35 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 29.1 | B | 8.2 | 27.3 | B | 7.8 | 27.4 | B | 7.8 |
| After 2 Days of Culture | 45.1 | C | 8.1 | 40.6 | C | 8.2 | 42.8 | C | 8.1 |
| After 3 Days of Culture | 50.8 | C | 7.9 | 53.7 | C | 8.1 | 52.5 | C | 8.2 |
| After 5 Days of Culture | 63.1 | C | 8.1 | 57.4 | C | 8.1 | 63.0 | C | 8.1 |

| | Comparative product 35 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 25.0 | B | 7.6 | 20.9 | B | 8.0 |
| After 2 Days of Culture | 46.5 | C | 8.4 | 44.4 | C | 8.1 |
| After 3 Days of Culture | 51.7 | C | 8.2 | 51.6 | C | 8.2 |
| After 5 Days of Culture | 59.7 | C | 8.3 | 58.1 | C | 7.9 |

TABLE 6-3-2

| | Comparative product 46 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 24.3 | B | 7.8 | 30.4 | B | 8.0 | 28.3 | B | 7.9 |
| After 2 Days of Culture | 39.7 | C | 7.9 | 45.3 | C | 8.1 | 45.2 | C | 8.2 |
| After 3 Days of Culture | 56.2 | C | 7.9 | 57.1 | C | 8.3 | 51.5 | C | 8.1 |
| After 5 Days of Culture | 57.9 | C | 8.1 | 66.0 | C | 8.2 | 62.7 | C | 8.1 |

| | Comparative product 46 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 20.4 | B | 7.7 | 23.4 | B | 8.0 |
| After 2 Days of Culture | 39.8 | C | 7.9 | 45.6 | C | 7.9 |
| After 3 Days of Culture | 46.7 | C | 8.1 | 54.5 | C | 8.0 |
| After 5 Days of Culture | 55.8 | C | 8.0 | 59.1 | C | 8.1 |

TABLE 6-3-3

| | Comparative product 49 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 27.4 | B | 8.0 | 20.2 | B | 7.9 | 25.6 | B | 8.2 |
| After 2 Days of Culture | 46.8 | C | 7.9 | 46.3 | C | 8.1 | 39.9 | C | 8.1 |
| After 3 Days of Culture | 50.1 | C | 8.1 | 46.1 | C | 8.1 | 51.0 | C | 8.2 |
| After 5 Days of Culture | 57.6 | C | 8.1 | 62.8 | C | 8.0 | 59.4 | C | 8.1 |

| | Comparative product 49 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 23.9 | B | 8.0 | 21.6 | B | 8.1 |
| After 2 Days of Culture | 41.5 | C | 8.1 | 34.6 | C | 8.2 |
| After 3 Days of Culture | 53.4 | C | 8.1 | 57.2 | C | 8.2 |
| After 5 Days of Culture | 64.2 | C | 8.1 | 59.3 | C | 8.3 |

TABLE 6-3-4

| | Comparative product 51 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 28.4 | B | 7.8 | 32.4 | B | 8.1 | 36.7 | B | 8.0 |
| After 2 Days of Culture | 46.0 | C | 7.6 | 40.9 | C | 7.9 | 40.1 | C | 8.1 |
| After 3 Days of Culture | 58.3 | C | 8.1 | 56.7 | C | 8.3 | 50.8 | C | 8.3 |
| After 5 Days of Culture | 66.3 | C | 8.0 | 60.7 | C | 8.1 | 62.3 | C | 8.1 |

| | Comparative product 51 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 32.5 | B | 8.0 | 30.0 | B | 7.9 |
| After 2 Days of Culture | 44.0 | C | 8.1 | 48.7 | C | 8.0 |
| After 3 Days of Culture | 51.6 | C | 8.2 | 55.2 | C | 8.2 |
| After 5 Days of Culture | 63.4 | C | 8.1 | 60.9 | C | 8.2 |

TABLE 6-3-5

| | Comparative product 56 Concentration of Component (A') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 29.5 | B | 8.0 | 33.3 | B | 8.1 | 31.1 | B | 8.0 |
| After 2 Days of Culture | 42.1 | C | 8.2 | 45.8 | C | 7.9 | 45.6 | C | 8.1 |
| After 3 Days of Culture | 53.4 | C | 8.1 | 51.6 | C | 8.1 | 51.7 | C | 8.3 |
| After 5 Days of Culture | 59.1 | C | 8.5 | 64.2 | C | 8.3 | 61.5 | C | 8.2 |

| | Comparative product 56 Concentration of Component (A') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 32.4 | B | 7.9 | 28.3 | B | 8.1 |
| After 2 Days of Culture | 46.2 | C | 8.1 | 43.5 | C | 8.2 |
| After 3 Days of Culture | 59.4 | C | 8.2 | 57.2 | C | 8.1 |
| After 5 Days of Culture | 61.3 | C | 8.3 | 66.0 | C | 8.0 |

*$\text{Log}_{10}\text{CFU/mL}$

From the above results, it was found that the example products employing the compounds represented by the Formula (2) can effectively inhibit biofilm formation.

(3) Examples Using the Compounds Represented by Formula (3)

Example 7

Blending of Biofilm Formation Inhibitor Compositions, and Verification of Ability to Inhibit Biofilm Formation Component (C) $R^3$—SH (C-31) C8 thiol [1-octanethiol, manufactured by Wako Pure Chemical Industries, Ltd., $R^3$=C8 alkyl]

(C-32) C10 thiol [1-decanethiol, manufactured by Wako Pure Chemical Industries, Ltd., $R^3$=C10 alkyl]

(C-33) C12 thiol [THIOKALCOL 20, manufactured by Kao Corporation, $R^3$=C12 alkyl]

(C-34) C12 thiol (tertiary) [t-dodecanethiol, manufactured by Wako Pure Chemical Industries, Ltd., $R^3$=C12 tertiary alkyl]

Component (C') $R^{3'}$-SH (C'-31) C3 thiol [L-propanethiol, manufactured by Wako Pure Chemical Industries, Ltd., $R^{3'}$=C3 alkyl]

(C'-32) C3 thiol (secondary) [2-propanethiol, manufactured by Wako Pure Chemical Industries, Ltd., $R^{3'}$=C3 alkyl]

(C'-33) C6 thiol [1-hexanethiol, manufactured by Wako Pure Chemical Industries, Ltd., $R^{3'}$=C6 alkyl]

(C'-34) C16 thiol [1-hexadecanethiol, manufactured by Wako Pure Chemical Industries, Ltd., $R^{3'}$=C16 alkyl]

(C'-35) C18 thiol [1-octadecanethiol, manufactured by Wako Pure Chemical Industries, Ltd., $R^{3'}$=C18 alkyl]

Component (B) surfactant [the number within the parentheses represents the average number of added moles of ethylene oxide]

<Anionic Surfactants>

(B-1) Sodium lauryl sulfate [EMAL 0, manufactured by Kao Corporation] (B-2) Sodium polyoxyethylene (2) lauryl ether sulfate [EMAL 20C, manufactured by Kao Corporation; active ingredient 25% by weight]

(B-3) Sodium polyoxyethylene (4.5) lauryl ether acetate [KAO AKYPO RLM45-NV, manufactured by Kao Corporation; active ingredient 24% by weight]

<Nonionic Surfactants>

(B-4) Polyoxyethylene (6) lauryl ether [EMULGEN 106, manufactured by Kao Corporation]

(B-5) Polyoxyethylene (12) lauryl ether [EMULGEN 120, manufactured by Kao Corporation]

(B-6) Lauryl glucoside [MYDOL 12, manufactured by Kao Corporation]

(B-7) Decyl glycerin monocaprylate [SY-GLYSTER MCA750, manufactured by SAKAMOTO YAKUHIN KOGYO CO., LTD.]

(B-8) Sorbitan monolaurate [RHEODOL SP-L10, manufactured by Kao Corporation]

(B-9) Polyoxyethylene (6) sorbitan monolaurate [RHEODOL TW-L106, manufactured by Kao Corporation]

(B-10) Polyoxyethylene (20) sorbitan monolaurate [RHEODOL TW-L120, manufactured by Kao Corporation]

The active ingredients were blended on a weight basis such that the concentration of the component (C) or component (C') was fixed at 1% by weight, while the concentration of the component (B) was selected from 1% by weight, 3% by weight, 6% by weight and 10% by weight, with the balance being ion-exchanged water. The blend was diluted using Mueller-Hinton Broth [manufactured by Nippon Becton Dickinson Co., Ltd.] to a concentration of 100 ppm of the component (C) or component (C'). The dilution was taken in an amount of 2 mL and placed on a 24-well microplate [manufactured by ASAHI TECHNO GLASS CORPORATION].

*Pseudomonas* (*Pseudomonas aeruginosa* NBRC 13275), *Serratia* (*Serratia marcescens* NBRC 12648), and *Klebsiella* (*Klebsiella pneumoniae* ATCC 13883) were each pre-cultured at 37 degrees Celsius for 24 hours using soybean-casein digest agar [SCD Agar Medium; manufactured by Nihon Pharmaceutical Co., Ltd.], to form colonies. A very small amount of bacterial clusters from the colonies formed was inoculated into each of the above-described test solutions on the microplate, using a sterilized bamboo skewer. The inoculated solution was incubated at 37 degrees Celsius for 48 hours, then the culture solution was discarded, and the state of formation of the biofilm adhering on the microplate wall was observed by visual evaluation. The state of the biofilm was graded such that the state in which the biofilm covered 0 to less than 20% of the microplate wall surface was graded A; the state in which the biofilm covered 20% or more to less than 40% of the wall surface was graded B; the state in which the biofilm covered 40% or more to less than 60% of the wall surface was graded C; and the state in which the biofilm covered 60% or more of the wall surface was graded D. The results are presented in Table 7-1 to Table 7-2.

TABLE 7-1

| | Example product 87 | Example product 88 | Example product 89 | Example product 90 | Example product 91 | Example product 92 | Example product 93 | Example product 94 |
|---|---|---|---|---|---|---|---|---|
| Component (C) | | | | | | | | |
| C-31 | 1.0 | 1.0 | 1.0 | 1.0 | | | | |
| C-32 | | | | | 1.0 | 1.0 | 1.0 | 1.0 |
| C-33 | | | | | | | | |
| C-34 | | | | | | | | |
| Surfactant (B) [Anionic Surfactant] | | | | | | | | |
| B-1 | 2.0 | | | | | | | |
| B-2 | | | | | | | 3.0 | |
| B-3 | | | | | | | | |

TABLE 7-1-continued

|  | | | | | | | | |
|---|---|---|---|---|---|---|---|---|
| [Nonionic Surfactant] | | | | | | | | |
| B-4 | | | | | 2.0 | | | |
| B-5 | | | | | | | | |
| B-6 | | 3.0 | | | | | | |
| B-7 | | | 6.0 | | | | | |
| B-8 | | | | | | | 6.0 | |
| B-9 | | | | 3.0 | | | | |
| B-10 | | | | | | | | 3.0 |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition | | | | | | | | |
| *P. aeruginosa* | B | B | B | B | A | A | A | A |
| *S. marcescens* | B | B | B | B | A | A | A | A |
| *K. pneumoniae* | B | B | B | B | A | A | A | A |

|  | Example product 95 | Example product 96 | Example product 97 | Example product 98 | Example product 99 | Example product 100 | Example product 101 | Example product 102 |
|---|---|---|---|---|---|---|---|---|
| Component (C) | | | | | | | | |
| C-31 | | | | | | | | |
| C-32 | | | | | | | | |
| C-33 | 1.0 | 1.0 | 1.0 | 1.0 | | | | |
| C-34 | | | | | 1.0 | 1.0 | 1.0 | 1.0 |
| Surfactant (B) | | | | | | | | |
| [Anionic Surfactant] | | | | | | | | |
| B-1 | | | | | | | | |
| B-2 | | | | | | | | |
| B-3 | | | | | | | | 6.0 |
| [Nonionic Surfactant] | | | | | | | | |
| B-4 | 3.0 | | | | 6.0 | | | |
| B-5 | | 6.0 | | | | 3.0 | | |
| B-6 | | | 3.0 | | | | | |
| B-7 | | | | | | | 3.0 | |
| B-8 | | | | | | | | |
| B-9 | | | | | | | | |
| B-10 | | | | 3.0 | | | | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition | | | | | | | | |
| *P. aeruginosa* | A | A | A | A | A | A | A | A |
| *S. marcescens* | A | A | A | A | A | A | A | A |
| *K. pneumoniae* | A | A | A | A | A | A | A | A |

TABLE 7-2

|  | Comparative Product 62 | Comparative Product 63 | Comparative Product 64 | Comparative Product 65 | Comparative Product 66 | Comparative Product 67 | Comparative Product 68 | Comparative Product 69 |
|---|---|---|---|---|---|---|---|---|
| Component (C') | | | | | | | | |
| C-31 | 1.0 | 1.0 | 1.0 | | | | | |
| C-32 | | | | 1.0 | 1.0 | 1.0 | | |

TABLE 7-2-continued

|  | (1) | (2) | (3) | (4) | (5) | (6) | (7) | (8) |
|---|---|---|---|---|---|---|---|---|
| C-33 |  |  |  |  |  |  | 1.0 | 1.0 |
| C-34 |  |  |  |  |  |  |  |  |
| C-35 |  |  |  |  |  |  |  |  |
| Surfactant (B) [Anionic Surfactant] |  |  |  |  |  |  |  |  |
| B-1 | 2.0 |  |  |  |  |  |  |  |
| B-2 |  |  |  | 2.0 |  |  |  |  |
| B-3 |  |  |  |  |  |  | 2.0 |  |
| [Nonionic Surfactant] |  |  |  |  |  |  |  |  |
| B-4 |  |  |  |  |  |  |  |  |
| B-5 |  | 3.0 |  |  |  |  |  | 6.0 |
| B-6 |  |  |  |  | 6.0 |  |  |  |
| B-7 |  |  | 3.0 |  |  |  |  |  |
| B-8 |  |  |  |  |  | 3.0 |  |  |
| B-9 |  |  |  |  |  |  |  |  |
| B-10 |  |  |  |  |  |  |  |  |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition |  |  |  |  |  |  |  |  |
| *P. aeruginosa* | D | D | D | D | D | D | D | D |
| *S. marcescens* | D | D | D | D | D | D | D | D |
| *K. pneumoniae* | D | D | D | D | D | D | D | D |

|  | Comparative Product 70 | Comparative Product 71 | Comparative Product 72 | Comparative Product 73 | Comparative Product 74 | Comparative Product 75 | Comparative Product 76 |
|---|---|---|---|---|---|---|---|
| Component (C') |  |  |  |  |  |  |  |
| C-31 |  |  |  |  |  |  |  |
| C-32 |  |  |  |  |  |  |  |
| C-33 | 1.0 |  |  |  |  |  |  |
| C-34 |  | 1.0 | 1.0 | 1.0 |  |  |  |
| C-35 |  |  |  |  | 1.0 | 1.0 | 1.0 |
| Surfactant (B) [Anionic Surfactant] |  |  |  |  |  |  |  |
| B-1 |  | 3.0 |  |  |  |  |  |
| B-2 |  |  |  |  |  |  |  |
| B-3 |  |  |  |  | 3.0 |  |  |
| [Nonionic Surfactant] |  |  |  |  |  |  |  |
| B-4 |  |  |  |  |  |  |  |
| B-5 |  |  |  |  |  |  |  |
| B-6 |  |  | 3.0 |  |  |  |  |
| B-7 |  |  |  |  |  | 6.0 |  |
| B-8 |  |  |  |  |  |  |  |
| B-9 | 3.0 |  |  |  |  |  |  |
| B-10 |  |  |  | 6.0 |  |  | 3.0 |
| Ion-Exchanged Water | Balance | Balance | Balance | Balance | Balance | Balance | Balance |
| Total | 100.0 | 100.0 | 100.0 | 100.0 | 100.0 | 100.0 | 100.0 |
| State of Biofilm Inhibition |  |  |  |  |  |  |  |
| *P. aeruginosa* | D | D | D | D | D | D | D |
| *S. marcescens* | D | D | D | D | D | D | D |
| *K. pneumoniae* | D | D | D | D | D | D | D |

Example 8

Test for Reduction of Biofilm Production in Large Volume Plastic Cup

Pseudomonas (*Pseudomonas aeruginosa* NBRC 13275) was pre-cultured at 37 degrees Celsius for 24 hours, using soybean-casein digest agar [SCD Agar Medium; manufactured by Nihon Pharmaceutical Co., Ltd.]. The colonies formed on the medium were scraped off and suspended in 10 mM sterile phosphate buffer (pH 7.2), and then the suspension was washed by centrifuging twice at 5,000×g for 15 minutes at 10 degrees Celsius. The resultant precipitate was again suspended in 10 mM sterile phosphate buffer (pH 7.2) to prepare a bacterial suspension in which the bacterial concentration was adjusted to 1.0 as the absorbance at 600 nm ($OD_{600}$=1.0). Thereafter, 100 mL of Mueller-Hinton Broth [manufactured by Nippon Becton Dickinson Co., Ltd.] and each of the 15 species of the test drugs selected from Example 7 were introduced into a 200-mL sterilized screw cup [manufactured by EIKENKIZAI CO., LTD.], and thoroughly mixed. The concentration of the component (C) or component (C') was adjusted to 5 ppm, 10 ppm, 50 ppm, 100 ppm or 500 ppm, and then 0.1 mL of the bacterial suspension prepared as described above was inoculated thereinto. Furthermore, as a control, a test section was simultaneously provided in which the bacteria were inoculated as described above into Mueller-Hinton Broth with no added drugs.

These were statically cultured at 37 degrees Celsius. At the designated time points of 1 day, 2 days, 3 days and 5 days after the initiation of culture, the number of bacterial cells in the culture solution was measured, and the biofilm formed inside the cup was observed by visual evaluation. Subsequently, the culture solution was centrifuged at 10,000×g for 30 minutes at 5 degrees Celsius, and the precipitate was removed, dried in a vacuum desiccator for 24 hours, and weighed, with the weight thus measured being taken as the weight of the biofilm produced in the culture solution. Furthermore, the state of the biofilm formation was graded such that the state in which no biofilm was confirmed in the cup was graded A; the state in which the formation of a biofilm started inside the cup at the air-liquid interface was graded B; and the state in which a biofilm was formed to extend from the air-liquid interface down to the culture solution was graded C.

The results are presented in Table 8-1-1 to Table 8-2-5.

TABLE 8-1-1

| | Control Concentration of Component (C) | | |
|---|---|---|---|
| | Amount of Biofilm (mg) | Visual Judgment of Biofilm | No of Bacterial Cells* |
| After 1 Day of Culture | 33.1 | B | 7.9 |
| After 2 Days of Culture | 48.7 | C | 8.2 |
| After 3 Days of Culture | 50.8 | C | 8.3 |
| After 5 Days of Culture | 62.6 | C | 8.2 |

TABLE 8-1-2

| | Example product 88 Concentration of Component (C) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 21.3 | B | 7.8 | 17.6 | B | 8.0 | 11.3 | A | 7.7 |
| After 2 Days of Culture | 25.4 | B | 7.8 | 22.2 | B | 8.0 | 18.0 | B | 7.9 |
| After 3 Days of Culture | 29.6 | B | 8.2 | 29.0 | B | 8.1 | 28.1 | B | 8.0 |
| After 5 Days of Culture | 30.7 | B | 8.1 | 32.8 | B | 8.0 | 30.2 | B | 7.9 |

| | Example product 88 Concentration of Component (C) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 10.9 | A | 7.8 | 10.3 | A | 7.8 |
| After 2 Days of Culture | 16.7 | B | 8.0 | 15.6 | B | 8.0 |
| After 3 Days of Culture | 20.7 | B | 8.2 | 19.7 | B | 7.9 |
| After 5 Days of Culture | 28.3 | B | 8.4 | 23.9 | B | 8.0 |

TABLE 8-1-3

| | Example product 91 Concentration of Component (C) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.5 | A | 7.7 | 1.7 | A | 7.6 | 1.9 | A | 7.3 |
| After 2 Days of Culture | 4.8 | A | 7.5 | 3.5 | A | 7.9 | 2.9 | A | 7.2 |
| After 3 Days of Culture | 19.7 | B | 7.9 | 9.7 | A | 7.7 | 4.3 | A | 7.6 |
| After 5 Days of Culture | 33.1 | B | 8.0 | 32.1 | B | 7.4 | 13.0 | A | 7.7 |

| | Example product 91 Concentration of Component (C) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 1.8 | A | 7.5 | 1.8 | A | 7.5 |
| After 2 Days of Culture | 3.3 | A | 7.4 | 2.5 | A | 7.4 |
| After 3 Days of Culture | 3.7 | A | 7.3 | 3.4 | A | 7.9 |
| After 5 Days of Culture | 6.2 | A | 7.8 | 5.5 | A | 7.8 |

TABLE 8-1-4

| | Example product 95 Concentration of Component (C) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.2 | A | 7.6 | 2.1 | A | 7.8 | 1.9 | A | 7.9 |
| After 2 Days of Culture | 5.3 | A | 7.8 | 3.3 | A | 7.9 | 3.8 | A | 7.9 |
| After 3 Days of Culture | 28.1 | B | 7.6 | 10.1 | A | 8.0 | 5.9 | A | 7.8 |
| After 5 Days of Culture | 35.0 | B | 7.4 | 31.6 | B | 7.8 | 13.7 | A | 7.9 |

| | Example product 95 Concentration of Component (C) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 1.5 | A | 7.5 | 2.0 | A | 7.8 |
| After 2 Days of Culture | 3.9 | A | 7.6 | 3.8 | A | 7.7 |
| After 3 Days of Culture | 5.5 | A | 7.9 | 5.2 | A | 7.8 |
| After 5 Days of Culture | 7.4 | A | 7.8 | 5.9 | A | 7.9 |

TABLE 8-1-5

| | Example product 100 Concentration of Component (C) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.7 | A | 7.7 | 2.0 | A | 7.4 | 2.4 | A | 7.8 |
| After 2 Days of Culture | 6.4 | A | 7.9 | 3.8 | A | 7.5 | 2.8 | A | 7.9 |
| After 3 Days of Culture | 24.8 | B | 7.6 | 10.6 | A | 7.6 | 6.3 | A | 7.7 |
| After 5 Days of Culture | 37.9 | B | 7.8 | 32.5 | B | 7.8 | 17.2 | B | 7.8 |

| | Example product 100 Concentration of Component (C) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.5 | A | 7.5 | 1.8 | A | 7.4 |
| After 2 Days of Culture | 2.3 | A | 7.7 | 3.8 | A | 7.6 |
| After 3 Days of Culture | 5.9 | A | 7.4 | 4.4 | A | 7.8 |
| After 5 Days of Culture | 12.0 | A | 7.3 | 8.2 | A | 7.8 |

*$\text{Log}_{10}\text{CFU/mL}$

TABLE 8-2-1

| | Comparative product 64 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 29.1 | B | 8.2 | 27.6 | B | 7.5 | 26.1 | B | 8.0 |
| After 2 Days of Culture | 44.7 | C | 7.8 | 42.4 | C | 8.4 | 49.8 | C | 8.1 |
| After 3 Days of Culture | 54.2 | C | 7.8 | 51.6 | C | 8.1 | 53.1 | C | 8.2 |
| After 5 Days of Culture | 64.2 | C | 8.1 | 60.2 | C | 8.2 | 63.8 | C | 8.1 |

| | Comparative product 64 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 26.5 | B | 8.0 | 23.8 | B | 8.1 |
| After 2 Days of Culture | 48.9 | C | 8.4 | 45.1 | C | 8.3 |
| After 3 Days of Culture | 58.1 | C | 8.4 | 52.1 | C | 8.2 |
| After 5 Days of Culture | 61.2 | C | 8.3 | 56.7 | C | 8.2 |

TABLE 8-2-2

| | Comparative product 66 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 22.1 | B | 8.0 | 30.8 | B | 7.9 | 25.1 | B | 7.8 |
| After 2 Days of Culture | 41.8 | C | 7.9 | 40.6 | C | 8.3 | 49.5 | C | 8.0 |
| After 3 Days of Culture | 53.1 | C | 8.1 | 54.1 | C | 8.2 | 52.6 | C | 8.2 |
| After 5 Days of Culture | 61.5 | C | 8.1 | 68.4 | C | 8.4 | 60.9 | C | 8.2 |

| | Comparative product 66 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 22.4 | B | 7.9 | 20.6 | B | 8.1 |
| After 2 Days of Culture | 45.2 | C | 8.1 | 42.9 | C | 8.3 |
| After 3 Days of Culture | 51.8 | C | 8.3 | 51.4 | C | 8.1 |
| After 5 Days of Culture | 62.3 | C | 8.7 | 57.4 | C | 8.4 |

TABLE 8-2-3

| | Comparative product 70 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 27.4 | B | 7.9 | 22.3 | B | 7.9 | 20.7 | B | 8.1 |
| After 2 Days of Culture | 45.2 | C | 8.0 | 49.8 | C | 8.1 | 47.6 | C | 8.2 |
| After 3 Days of Culture | 51.6 | C | 8.6 | 59.6 | C | 8.2 | 52.4 | C | 8.4 |
| After 5 Days of Culture | 60.7 | C | 8.4 | 60.7 | C | 8.3 | 59.1 | C | 8.2 |

| | Comparative product 70 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 25.3 | B | 8.0 | 21.3 | B | 8.2 |
| After 2 Days of Culture | 46.2 | C | 8.1 | 40.8 | C | 8.2 |
| After 3 Days of Culture | 55.8 | C | 8.3 | 52.6 | C | 8.3 |
| After 5 Days of Culture | 65.0 | C | 8.3 | 61.7 | C | 8.5 |

TABLE 8-2-4

| | Comparative product 71 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 30.2 | B | 7.9 | 33.5 | B | 7.7 | 33.6 | B | 8.1 |
| After 2 Days of Culture | 44.7 | C | 8.1 | 48.6 | C | 7.9 | 45.2 | C | 8.1 |
| After 3 Days of Culture | 59.2 | C | 8.3 | 56.2 | C | 8.3 | 56.8 | C | 8.2 |
| After 5 Days of Culture | 62.5 | C | 8.2 | 61.2 | C | 8.3 | 61.5 | C | 8.3 |

| | Comparative product 71 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 25.1 | B | 8.1 | 25.7 | B | 8.1 |
| After 2 Days of Culture | 44.3 | C | 8.2 | 50.6 | C | 8.1 |
| After 3 Days of Culture | 58.7 | C | 8.1 | 57.0 | C | 8.2 |
| After 5 Days of Culture | 66.8 | C | 8.3 | 62.0 | C | 8.1 |

TABLE 8-2-5

| | Comparative product 75 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 32.5 | B | 8.2 | 31.9 | B | 8.0 | 31.5 | B | 8.0 |
| After 2 Days of Culture | 46.8 | C | 8.2 | 47.4 | C | 7.9 | 44.7 | C | 8.1 |
| After 3 Days of Culture | 56.9 | C | 8.1 | 55.1 | C | 8.2 | 56.8 | C | 8.2 |
| After 5 Days of Culture | 61.4 | C | 8.0 | 68.9 | C | 8.1 | 63.4 | C | 8.1 |

| | Comparative product 75 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 32.8 | B | 7.8 | 33.9 | B | 8.1 |
| After 2 Days of Culture | 50.0 | C | 8.2 | 49.9 | C | 8.3 |
| After 3 Days of Culture | 58.3 | C | 8.5 | 57.2 | C | 8.2 |
| After 5 Days of Culture | 65.2 | C | 8.4 | 67.7 | C | 8.2 |

*$\text{Log}_{10}\text{CFU/mL}$

From the above results, it was found that the example products containing the compounds represented by the Formula (3) can effectively inhibit biofilm formation on a long-term basis.

(4) Examples Using the Compounds Represented by Formula (4)

Example 9

Blending of Biofilm Formation Inhibitor Compositions, and Verification of Ability to Inhibit Biofilm Formation Component (C) $R^{40}$—CO—CH$_3$ (C-41) C8 alcohol-acetic acid ester [octyl acetate, manufactured by Wako Pure Chemical Industries, Ltd., $R^4$=C8 alkyl]

(C-42) C10 alcohol-acetic acid ester [decyl acetate, manufactured by Wako Pure Chemical Industries, Ltd., $R^4$=C10 alkyl] (C-43) C12 alcohol-acetic acid ester [dodecyl acetate, manufactured by Wako Pure Chemical Industries, Ltd., $R^4$=C12 alkyl]

Component (C') $R^{4'}$O—CO—CH$_3$ (C'-41) C2 alcohol-acetic acid ester [ethyl acetate, manufactured by Wako Pure Chemical Industries, Ltd., $R^{4'}$=C2 alkyl]

(C'-42) C4 alcohol-acetic acid ester [butyl acetate, manufactured by Wako Pure Chemical Industries, Ltd., $R^{4'}$=C4 alkyl]

(C'-43) C6 alcohol-acetic acid ester [hexyl acetate, manufactured by Wako Pure Chemical Industries, Ltd., $R^{4'}$=C6 alkyl]

(C'-44) C16 alcohol-acetic acid ester [hexadecyl acetate, manufactured by Wako Pure Chemical Industries, Ltd., $R^{4'}$=C16 alkyl]

(C'-45) C18 alcohol-acetic acid ester [octadecyl acetate, manufactured by Wako Pure Chemical Industries, Ltd., $R^{4'}$=C18 alkyl]

Component (B) surfactant [the number within the parentheses represents the average number of added moles of ethylene oxide]

<Anionic Surfactants>

(B-1) Sodium lauryl sulfate [EMAL 0, manufactured by Kao Corporation]

(B-2) Sodium polyoxyethylene (2) lauryl ether sulfate [EMAL 20C, manufactured by Kao Corporation; active ingredient 25% by weight]

(B-3) Sodium polyoxyethylene (4.5) lauryl ether acetate [KAO AKYPO RLM45-NV, manufactured by Kao Corporation; active ingredient 24% by weight]

<Nonionic Surfactants>

(B-4) Polyoxyethylene (6) lauryl ether [EMULGEN 106, manufactured by Kao Corporation]

(B-5) Polyoxyethylene (12) lauryl ether [EMULGEN 120, manufactured by Kao Corporation]

(B-6) Lauryl glucoside [MYDOL 12, manufactured by Kao Corporation]

(B-7) Decyl glycerin monocaprylate [SY-GLYSTER MCA750, manufactured by SAKAMOTO YAKUHIN KOGYO CO., LTD.]

(B-8) Sorbitan monolaurate [RHEODOL SP-L10, manufactured by Kao Corporation]

(B-9) Polyoxyethylene (6) sorbitan monolaurate [RHEODOL TW-L106, manufactured by Kao Corporation]

(B-10) Polyoxyethylene (20) sorbitan monolaurate [RHEODOL TW-L120, manufactured by Kao Corporation]

The active ingredients were blended on a weight basis such that the concentration of the component (C) or component (C') was fixed at 1% by weight, while the concentration of the component (B) was selected from 1% by weight, 3% by weight, 6% by weight and 10% by weight, with the balance being ion-exchanged water. The blend was diluted using Mueller-Hinton Broth [manufactured by Nippon Becton Dickinson Co., Ltd.] to a concentration of 100 ppm of the component (C) or component (C'). The dilution was taken in an amount of 2 mL and placed on a 24-well microplate [manufactured by ASAHI TECHNO GLASS CORPORATION].

*Pseudomonas* (*Pseudomonas aeruginosa* NBRC 13275), *Serratia* (*Serratia marcescens* NBRC 12648), and *Klebsiella* (*Klebsiella pneumoniae* ATCC 13883) were each pre-cultured at 37 degrees Celsius for 24 hours using soybean-casein digest agar [SCD Agar Medium; manufactured by Nihon Pharmaceutical Co., Ltd.], to form colonies. A very small amount of bacterial clusters from the colonies formed was inoculated into each of the above-described test solutions on the microplate, using a sterilized bamboo skewer. The inoculated solution was incubated at 37 degrees Celsius for 48 hours, then the culture solution was discarded, and the state of formation of the biofilm adhering on the microplate wall was observed by visual evaluation. The state of the biofilm was graded such that the state in which the biofilm covered 0 to less than 20% of the microplate wall surface was graded A; the state in which the biofilm covered 20% or more to less than 40% of the wall surface was graded B; the state in which the biofilm covered 40% or more to less than 60% of the wall surface was graded C; and the state in which the biofilm covered 60% or more of the wall surface was graded D. The results are presented in Table 9-1 to Table 9-2.

TABLE 9-1

| | Example product 103 | Example product 104 | Example product 105 | Example product 106 | Example product 107 | Example product 108 | Example product 109 | Example product 110 | Example product 111 | Example product 112 | Example product 113 | Example product 114 |
|---|---|---|---|---|---|---|---|---|---|---|---|---|
| Component (C) | | | | | | | | | | | | |
| C-41 | 1.0 | 1.0 | 1.0 | 1.0 | | | | | | | | |
| C-42 | | | | | 1.0 | 1.0 | 1.0 | 1.0 | | | | |
| C-43 | | | | | | | | | 1.0 | 1.0 | 1.0 | 1.0 |

TABLE 9-1-continued

| | Example product 103 | Example product 104 | Example product 105 | Example product 106 | Example product 107 | Example product 108 | Example product 109 | Example product 110 | Example product 111 | Example product 112 | Example product 113 | Example product 114 |
|---|---|---|---|---|---|---|---|---|---|---|---|---|
| Surfactant (B) [Anionic Surfactant] | | | | | | | | | | | | |
| B-1 | | 3.0 | | | | | | | | | | |
| B-2 | | | | | | 3.0 | | | | | | |
| B-3 | | | | | | | | | | | | 3.0 |
| [Nonionic Surfactant] | | | | | | | | | | | | |
| B-4 | | | | | 3.0 | | | | 6.0 | | | |
| B-5 | 3.0 | | | | | | | | | 3.0 | | |
| B-6 | | | | | | | | | | | 3.0 | |
| B-7 | | | 3.0 | | | | | | | | | |
| B-8 | | | | | | | 3.0 | | | | | |
| B-9 | | | | 6.0 | | | | | | | | |
| B-10 | | | | | | | | 3.0 | | | | |
| Ion-Exchanged Water | Balance | Balance | Balance | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 | 100.0 | 100.0 | 100.0 |
| State of Biofilm Inhibition | | | | | | | | | | | | |
| *P. aeruginosa* | B | B | B | B | A | A | A | A | A | A | A | A |
| *S. marcescens* | B | B | B | B | A | A | A | A | A | A | A | A |
| *K. pneumoniae* | B | B | B | B | A | A | A | A | A | A | A | A |

TABLE 9-2

| | Comparative Product 77 | Comparative Product 78 | Comparative Product 79 | Comparative Product 80 | Comparative Product 81 | Comparative Product 82 | Comparative Product 83 | Comparative Product 84 |
|---|---|---|---|---|---|---|---|---|
| Component (C) | | | | | | | | |
| C'-41 | 1.0 | 1.0 | 1.0 | | | | | |
| C'-42 | | | | 1.0 | 1.0 | 1.0 | | |
| C'-43 | | | | | | | 1.0 | 1.0 |
| C'-44 | | | | | | | | |
| C'-45 | | | | | | | | |
| Surfactant (B) [Anionic Surfactant] | | | | | | | | |
| B-1 | 3.0 | | | | | | | |
| B-2 | | | | 3.0 | | | | |
| B-3 | | | | | | | 6.0 | |
| [Nonionic Surfactant] | | | | | | | | |
| B-4 | | | | | | | | |
| B-5 | | 3.0 | | | | | | 6.0 |
| B-6 | | | | | 3.0 | | | |
| B-7 | | | | | | 3.0 | | |
| B-8 | | | 3.0 | | | | | |
| B-9 | | | | | | | | |
| B-10 | | | | | | | | |
| Ion-Exchanged Water | Balance | Balance | Balance | Balance | Balance | Balance | Balance | Balance |
| Total | 100.0 | 100.0 | 100.0 | 100.0 | 100.0 | 100.0 | 100.0 | 100.0 |
| State of Biofilm Inhibition | | | | | | | | |
| *P. aeruginosa* | D | D | D | D | D | D | D | D |
| *S. marcescens* | D | D | D | D | D | D | D | D |
| *K. pneumoniae* | D | D | D | D | D | D | D | D |

TABLE 9-2-continued

| | Comparative Product 85 | Comparative Product 86 | Comparative Product 87 | Comparative Product 88 | Comparative Product 89 | Comparative Product 90 | Comparative Product 91 |
|---|---|---|---|---|---|---|---|
| Component (C) | | | | | | | |
| C'-41 | | | | | | | |
| C'-42 | | | | | | | |
| C'-43 | 1.0 | | | | | | |
| C'-44 | | 1.0 | 1.0 | 1.0 | | | |
| C'-45 | | | | | 1.0 | 1.0 | 1.0 |
| Surfactant (B) [Anionic Surfactant] | | | | | | | |
| B-1 | | 6.0 | | | | | |
| B-2 | | | | | | | |
| B-3 | | | | | 3.0 | | |
| [Nonionic Surfactant] | | | | | | | |
| B-4 | | | | | | | |
| B-5 | | | | | | | |
| B-6 | | | 3.0 | | | | |
| B-7 | | | | | | 3.0 | |
| B-8 | | | | | | | |
| B-9 | 3.0 | | | | | | |
| B-10 | | | | 3.0 | | | 3.0 |
| Ion-Exchanged Water | Balance | Balance | Balance | Balance | Balance | Balance | Balance |
| Total | 100.0 | 100.0 | 100.0 | 100.0 | 100.0 | 100.0 | 100.0 |
| State of Biofilm Inhibition | | | | | | | |
| P. aeruginosa | D | D | D | D | D | D | D |
| S. marcescens | D | D | D | D | D | D | D |
| K. pneumoniae | D | D | D | D | D | D | D |

Example 10

Test for Reduction of Biofilm Production in Large Volume Plastic Cup

Pseudomonas (Pseudomonas aeruginosa NBRC 13275) was pre-cultured at 37 degrees Celsius for 24 hours, using soybean-casein digest agar [SCD Agar Medium; manufactured by Nihon Pharmaceutical Co., Ltd.]. The colonies formed on the medium were scraped off and suspended in 10 mM sterile phosphate buffer (pH 7.2), and then the suspension was washed by centrifuging twice at 5,000×g for 15 minutes at 10 degrees Celsius. The resultant precipitate was again suspended in 10 mM sterile phosphate buffer (pH 7.2) to prepare a bacterial suspension in which the bacterial concentration was adjusted to 1.0 as the absorbance at 600 nm ($OD_{600}$=1.0). Thereafter, 100 mL of Mueller-Hinton Broth [manufactured by Nippon Becton Dickinson Co., Ltd.] and each of the 15 species of the test drugs selected in Example 9 were introduced into a 200-mL sterilized screw cup [manufactured by EIKENKIZAI CO., LTD.], and thoroughly mixed. The concentration of the component (C) or component (C') was adjusted to 5 ppm, 10 ppm, 50 ppm, 100 ppm or 500 ppm, and then 0.1 mL of the bacterial suspension prepared as described above was inoculated thereinto. Furthermore, as a control, a test section was simultaneously provided in which the bacteria were inoculated as described above into Mueller-Hinton Broth with no added drugs.

These were statically cultured at 37 degrees Celsius. At the designated time points of 1 day, 2 days, 3 days and 5 days after the initiation of culture, the number of bacterial cells in the culture solution was measured, and the biofilm formed inside the cup was observed by visual evaluation. Subsequently, the culture solution was centrifuged at 10,000×g for 30 minutes at 5 degrees Celsius, and the precipitate was removed, dried in a vacuum desiccator for 24 hours, and weighed, with the weight thus measured being taken as the weight of the biofilm produced in the culture solution. Furthermore, the state of the biofilm formation was graded such that the state in which no biofilm was confirmed in the cup was graded A; the state in which the formation of a biofilm started inside the cup at the air-liquid interface was graded B; and the state in which a biofilm was formed to extend from the air-liquid interface down to the culture solution was graded C.

The results are presented in Table 10-1-1 to Table 10-2-5.

TABLE 10-1-1

| | Control | | |
|---|---|---|---|
| Concentration of Component (C) | Amount of Biofilm (mg) | Visual Judgment of Biofilm | No. of Bacterial Cells* |
| After 1 Day of Culture | 33.1 | B | 7.9 |
| After 2 Days of Culture | 48.7 | C | 8.2 |
| After 3 Days of Culture | 50.8 | C | 8.3 |
| After 5 Days of Culture | 62.6 | C | 8.2 |

TABLE 10-1-2

| | Example product 103 Concentration of Component (C) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 22.8 | B | 7.9 | 18.4 | B | 8.1 | 10.8 | A | 7.8 |
| After 2 Days of Culture | 24.6 | B | 7.8 | 23.1 | B | 8.0 | 17.6 | B | 8.0 |
| After 3 Days of Culture | 30.1 | B | 8.2 | 29.7 | B | 8.0 | 23.4 | B | 7.9 |
| After 5 Days of Culture | 32.7 | B | 8.2 | 31.5 | B | 7.9 | 31.7 | B | 7.8 |

| | Example product 103 Concentration of Component (C) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 11.0 | A | 7.9 | 10.8 | A | 7.9 |
| After 2 Days of Culture | 15.8 | B | 7.9 | 16.8 | B | 8.0 |
| After 3 Days of Culture | 21.0 | B | 8.1 | 20.6 | B | 7.9 |
| After 5 Days of Culture | 27.6 | B | 8.2 | 22.5 | B | 8.1 |

TABLE 10-1-3

| | Example product 107 Concentration of Component (C) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 3.2 | A | 7.8 | 2.1 | A | 7.8 | 1.9 | A | 7.6 |
| After 2 Days of Culture | 5.1 | A | 7.8 | 3.6 | A | 7.9 | 3.8 | A | 7.5 |
| After 3 Days of Culture | 20.0 | B | 7.7 | 9.9 | A | 7.8 | 5.1 | A | 7.7 |
| After 5 Days of Culture | 31.8 | B | 7.6 | 33.5 | B | 7.9 | 15.0 | A | 7.9 |

| | Example product 107 Concentration of Component (C) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.0 | A | 7.6 | 1.9 | A | 7.8 |
| After 2 Days of Culture | 3.9 | A | 7.5 | 2.8 | A | 7.6 |
| After 3 Days of Culture | 4.1 | A | 7.5 | 3.6 | A | 7.8 |
| After 5 Days of Culture | 7.2 | A | 7.9 | 5.9 | A | 7.7 |

TABLE 10-1-4

| | Example product 112 Concentration of Component (A) | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.8 | A | 7.8 | 2.0 | A | 7.4 | 2.6 | A | 7.9 |
| After 2 Days of Culture | 6.8 | A | 7.9 | 3.4 | A | 7.7 | 2.9 | A | 7.8 |
| After 3 Days of Culture | 25.3 | B | 8.0 | 11.5 | A | 7.8 | 7.1 | A | 7.7 |
| After 5 Days of Culture | 38.1 | B | 8.1 | 35.0 | B | 7.8 | 18.3 | B | 7.6 |

| | Example product 112 Concentration of Component (A) | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 2.2 | A | 7.6 | 1.7 | A | 7.6 |
| After 2 Days of Culture | 2.6 | A | 7.8 | 3.6 | A | 7.4 |
| After 3 Days of Culture | 6.2 | A | 7.5 | 4.8 | A | 7.9 |
| After 5 Days of Culture | 13.8 | A | 7.4 | 9.2 | A | 7.9 |

*$\text{Log}_{10}\text{CFU/mL}$

TABLE 10-2-1

| | Comparative product 78 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 30.2 | B | 8.1 | 28.4 | B | 7.8 | 25.1 | B | 8.0 |
| After 2 Days of Culture | 45.1 | C | 7.9 | 41.6 | C | 8.0 | 50.0 | C | 8.2 |
| After 3 Days of Culture | 53.6 | C | 7.9 | 50.9 | C | 7.9 | 51.4 | C | 8.0 |
| After 5 Days of Culture | 63.8 | C | 7.8 | 61.7 | C | 8.1 | 61.6 | C | 8.3 |

| | Comparative product 78 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 25.6 | B | 7.8 | 22.4 | B | 8.0 |
| After 2 Days of Culture | 49.1 | C | 8.1 | 44.9 | C | 8.3 |
| After 3 Days of Culture | 54.6 | C | 8.1 | 51.6 | C | 8.1 |
| After 5 Days of Culture | 59.8 | C | 8.2 | 58.4 | C | 8.2 |

TABLE 10-2-2

| | Comparative product 81 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 20.8 | B | 7.9 | 29.7 | B | 8.0 | 21.8 | B | 7.9 |
| After 2 Days of Culture | 40.5 | C | 7.9 | 42.1 | C | 8.2 | 46.2 | C | 8.1 |
| After 3 Days of Culture | 52.4 | C | 8.0 | 50.7 | C | 8.1 | 50.8 | C | 8.4 |
| After 5 Days of Culture | 63.8 | C | 8.2 | 64.3 | C | 8.1 | 59.7 | C | 8.1 |

| | Comparative product 81 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 21.5 | B | 8.1 | 18.7 | B | 8.0 |
| After 2 Days of Culture | 43.2 | C | 8.3 | 36.8 | C | 8.1 |
| After 3 Days of Culture | 50.7 | C | 8.3 | 49.6 | C | 8.6 |
| After 5 Days of Culture | 61.4 | C | 8.5 | 58.8 | C | 8.5 |

TABLE 10-2-3

| | Comparative product 83 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 25.6 | B | 8.0 | 21.7 | B | 7.9 | 19.3 | B | 7.9 |
| After 2 Days of Culture | 44.7 | C | 8.1 | 48.6 | C | 8.1 | 42.1 | C | 8.1 |
| After 3 Days of Culture | 52.4 | C | 8.3 | 60.3 | C | 8.5 | 50.9 | C | 8.2 |
| After 5 Days of Culture | 58.6 | C | 8.2 | 62.8 | C | 8.4 | 58.3 | C | 8.4 |

| | Comparative product 83 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 23.6 | B | 8.0 | 20.9 | B | 8.0 |
| After 2 Days of Culture | 42.7 | C | 8.2 | 41.3 | C | 8.1 |
| After 3 Days of Culture | 53.4 | C | 8.3 | 52.4 | C | 8.1 |
| After 5 Days of Culture | 63.5 | C | 8.1 | 64.2 | C | 8.2 |

TABLE 10-2-4

| | Comparative product 87 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 29.1 | B | 7.8 | 32.8 | B | 7.9 | 35.8 | B | 8.0 |
| After 2 Days of Culture | 45.3 | C | 7.9 | 46.1 | C | 7.9 | 44.6 | C | 7.9 |
| After 3 Days of Culture | 54.2 | C | 8.0 | 55.9 | C | 8.1 | 53.1 | C | 8.1 |
| After 5 Days of Culture | 61.2 | C | 8.2 | 60.2 | C | 8.2 | 60.7 | C | 8.3 |

| | Comparative product 87 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 29.4 | B | 8.0 | 25.7 | B | 8.2 |
| After 2 Days of Culture | 42.6 | C | 8.1 | 50.6 | C | 8.3 |
| After 3 Days of Culture | 56.1 | C | 8.3 | 57.0 | C | 8.1 |
| After 5 Days of Culture | 66.8 | C | 8.1 | 62.0 | C | 8.2 |

TABLE 10-2-5

| | Comparative product 91 Concentration of Component (C') | | | | | | | | |
|---|---|---|---|---|---|---|---|---|---|
| | 5 ppm | | | 10 ppm | | | 50 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 32.5 | B | 8.1 | 32.1 | B | 7.9 | 32.8 | B | 8.0 |
| After 2 Days of Culture | 44.1 | C | 8.2 | 45.2 | C | 8.1 | 46.8 | C | 8.2 |
| After 3 Days of Culture | 56.8 | C | 8.0 | 57.6 | C | 8.0 | 55.2 | C | 8.1 |
| After 5 Days of Culture | 62.0 | C | 8.1 | 67.4 | C | 8.3 | 62.7 | C | 8.3 |

| | Comparative product 91 Concentration of Component (C') | | | | | |
|---|---|---|---|---|---|---|
| | 100 ppm | | | 500 ppm | | |
| | Amount of Biofilm (mg) | Visual Judgment of Biofilm | No. of Bacterial Cells* | Amount of Biofilm (mg) | Visual Judgment of Biofilm | No. of Bacterial Cells* |
| After 1 Day of Culture | 34.0 | B | 7.9 | 32.8 | B | 8.0 |
| After 2 Days of Culture | 48.3 | C | 8.1 | 50.7 | C | 8.2 |
| After 3 Days of Culture | 51.6 | C | 8.3 | 56.4 | C | 8.1 |
| After 5 Days of Culture | 63.1 | C | 8.2 | 65.1 | C | 8.3 |

*$\mathrm{Log}_{10}\mathrm{CFU/mL}$

From the above results, it was found that the example products containing the compounds represented by the Formula (4) can effectively inhibit biofilm formation on a long-term basis.

The invention claimed is:

1. A method of inhibiting biofilm formation, which method comprises:

contacting a biofilm formation inhibitor composition with microorganisms, wherein the biofilm formation inhibitor composition comprises the following component (A):

(A) at least one or more selected from compounds represented by Formula (1) and Formula (2) or a salt thereof:

$$R^1O\text{---}(EO)_p\text{---}H \quad (1)$$

$$R^2\text{---}N\begin{pmatrix}(EO)_m\text{---}H\\(EO)_n\text{---}H\end{pmatrix} \quad (2)$$

wherein $R^1$ and $R^2$, which are identical or different, each represents an alkyl group or an alkenyl group, which is a straight chain or branched chain having 8 to 14 carbon atoms; EO represents an ethyleneoxy group; p represents an integer from 1 to 5; and m and n are each an average number of added moles, with m+n being a number from 2 to 30; and (B) a surfactant;

wherein the weight ratio of the component (A) and the component (B), (A)/(B), is not more than 2.

2. The method of inhibiting biofilm formation according to claim 1, wherein the contact between the biofilm formation inhibitor composition and microorganisms is carried out continuously.

3. The method of inhibiting biofilm formation according to claim 1, wherein the concentration by weight of the component (A) at the time of use of the biofilm formation inhibitor composition is 1 to 10,000 ppm.

4. The method according to claim 1, wherein the component (B) surfactant is at least one or more selected from the group consisting of anionic surfactants, and nonionic surfactants other than the component (A).

* * * * *